United States Patent
Mazet et al.

(10) Patent No.: US 11,039,588 B2
(45) Date of Patent: Jun. 22, 2021

(54) RESISTANCE TO TOLCNDV IN SQUASH

(71) Applicant: Vilmorin & Cie, Paris (FR)

(72) Inventors: Julien Mazet, Saint-Rémy-de-Provence (FR); Juan Aguilar, Almeria (ES); Isabelle Justafre, Saint-Rémy-de-Provence (FR); Eric Lionneton, La Bohalle (FR)

(73) Assignee: Vilmorin & Cie, Paris (FR)

( * ) Notice: Subject to any disclaimer, the term of this patent is extended or adjusted under 35 U.S.C. 154(b) by 153 days.

(21) Appl. No.: 15/775,109

(22) PCT Filed: Nov. 10, 2016

(86) PCT No.: PCT/EP2016/077352
§ 371 (c)(1),
(2) Date: May 10, 2018

(87) PCT Pub. No.: WO2017/081205
PCT Pub. Date: May 18, 2017

(65) Prior Publication Data
US 2019/0380292 A1    Dec. 19, 2019

Related U.S. Application Data

(60) Provisional application No. 62/253,427, filed on Nov. 10, 2015.

(51) Int. Cl.
| | |
|---|---|
| *A01H 1/00* | (2006.01) |
| *A01H 6/34* | (2018.01) |
| *A01H 5/08* | (2018.01) |
| *C12Q 1/6895* | (2018.01) |
| *A01H 1/04* | (2006.01) |

(52) U.S. Cl.
CPC ............ *A01H 1/126* (2021.01); *A01H 1/045* (2021.01); *A01H 5/08* (2013.01); *A01H 6/348* (2018.05); *C12Q 1/6895* (2013.01)

(58) Field of Classification Search
None
See application file for complete search history.

(56) References Cited

U.S. PATENT DOCUMENTS

2011/0138493 A1* 6/2011 Copes .................. A01H 3/00
800/265

FOREIGN PATENT DOCUMENTS

WO    WO2004/101798 A2    11/2004

OTHER PUBLICATIONS

Kistler et al, 2015, PNAS 49:15107-15112.*
Della Vecchia et al (1993, Cucurbit Genetics Cooperative Report 16:70-72).*
Rakha et al (2012, World Appl. Sci. J. 20:1366-1370).*
Lopez et al (Euphytica 204:679-691).*
International Search Report in International Patent Application No. PCT/EP2016/077352, dated May 18, 2017.
Written Opinion in International Patent Application No. PCT/EP2016/077352, dated May 18, 2017.
Juarez et al. "first Detection of Tomato leaf curl New Delhi virus Infecting Zucchini in Spain", *Plant Disease, The American Phytopathological Society*, 98(6):857, Jun. 2014; and related gene bank sequence EM_STD:KF749223, Mar. 2014.
Rai et al., "Identification and validation of an ISSR marker linked to Tomato leaf curl New Delhi virus resistant gene in a core set of tomato accessions" *Vegetable Science* 40(1):Jan. 1, 2013.
Mnari-Hattab et al. "New Disease Reports First report of Tomato leaf curl New Delhi virus infecting cucurbits in Tunisia", Jan. 2015, retrieved from internet: https://www.ndrs.org.uk/pdfs/031/NDR_031021.pdf.
Dsmz et al. "Data Sheet on Tomato leaf curl New Delhi virus (ToLCNDV)", Leibniz-Insitut DSMZ-Deusche Sammlung, Jun. 2015, retrieved from internet: http://www.dsmz.de/uploads/media/ToLCNDC-ELISA.pdf.
Pachner et al., "Phenotypic and marker-assisted pyramiding of genes resistance to zucchini yellow mosaic virus in oilseed pumpkin (*Cucurbita pepo*)" *Plant Breeding*, 134(1):121-128, Dec. 2014.
Bandaranayake et al., "Molecular detection and characterization of begomoviruses associated with cucurbitaceae vegetable in Sri Lanka" *Journal of the National Science Foundation*, 42(3): 265-271, Sep. 2014.
Panno et al., "New Disease Reports First report of Tomato leaf curl New Delhi virus affecting zucchini squash in an important horticultural area of southern Italy", Feb. 2016, retrieved from internet: https://www.ndrs.org.uk/pdfs/033/NDR_022005.pdf.
Paris et al, 1988, Single-gene resistance to zucchini yellow mosaic virus in *Cucurbita moschata*, Euphytica: vol. 37, pp. 27-29.

\* cited by examiner

*Primary Examiner* — Anne Kubelik
(74) *Attorney, Agent, or Firm* — Cooley LLP

(57) ABSTRACT

The invention provides a Tomato Leaf Curl New Dehli Virus (ToLCNDV) tolerance or resistant QTL in cucurbit plants and plants comprising the QTL. The invention also provides molecular markers linked to QTL. The invention further provides methods of breeding to produce plants that are resistant to ToLCNDV, and the resistant plants produced by such methods.

12 Claims, 5 Drawing Sheets
Specification includes a Sequence Listing.

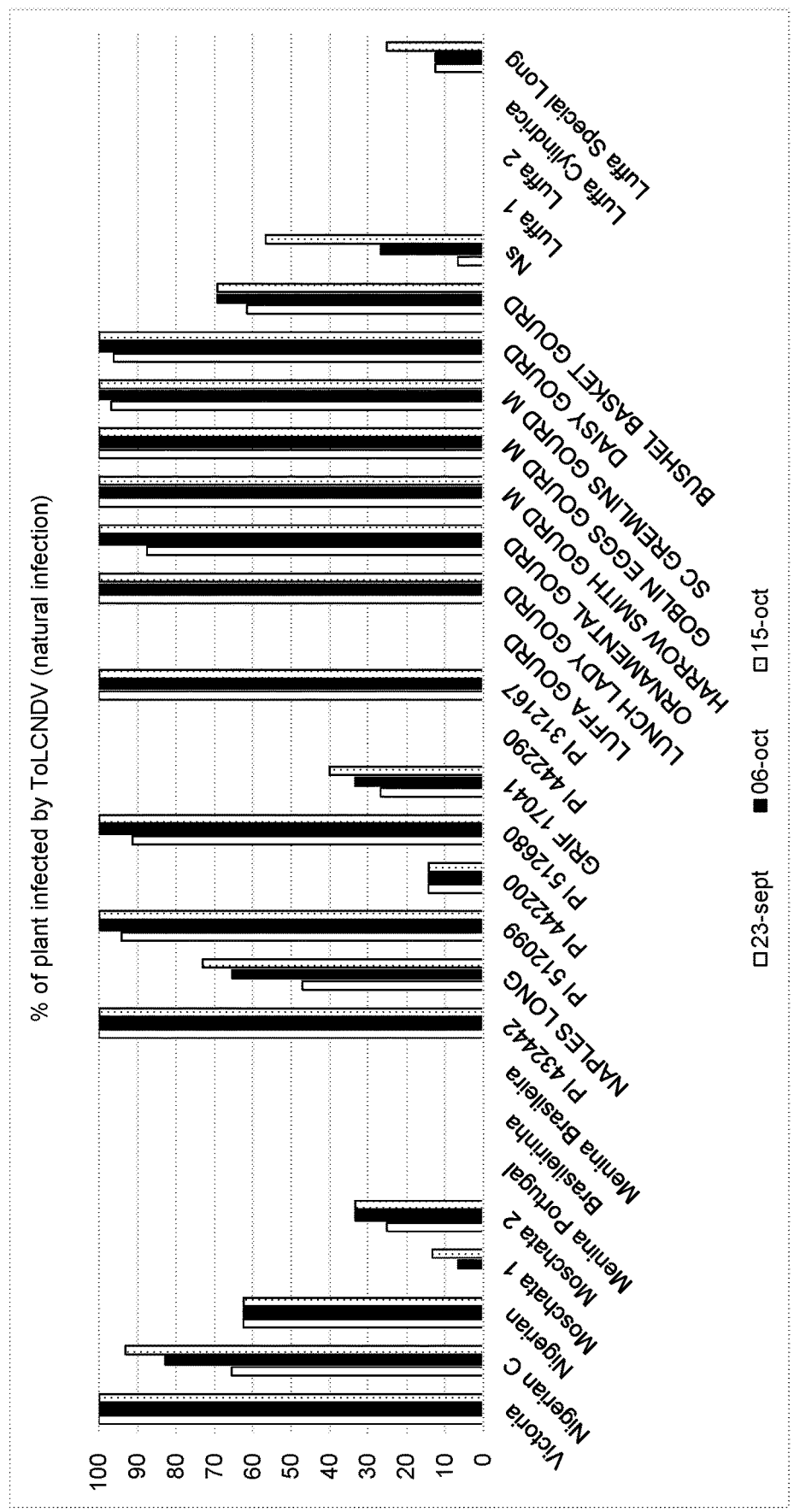
Figure 1. Percentage of infected plants among the four replication for each accession tested. In white: evaluation done on sept-23rd; in dark: evaluation done on oct-06th; in dotted: evaluation done on oct-15th.

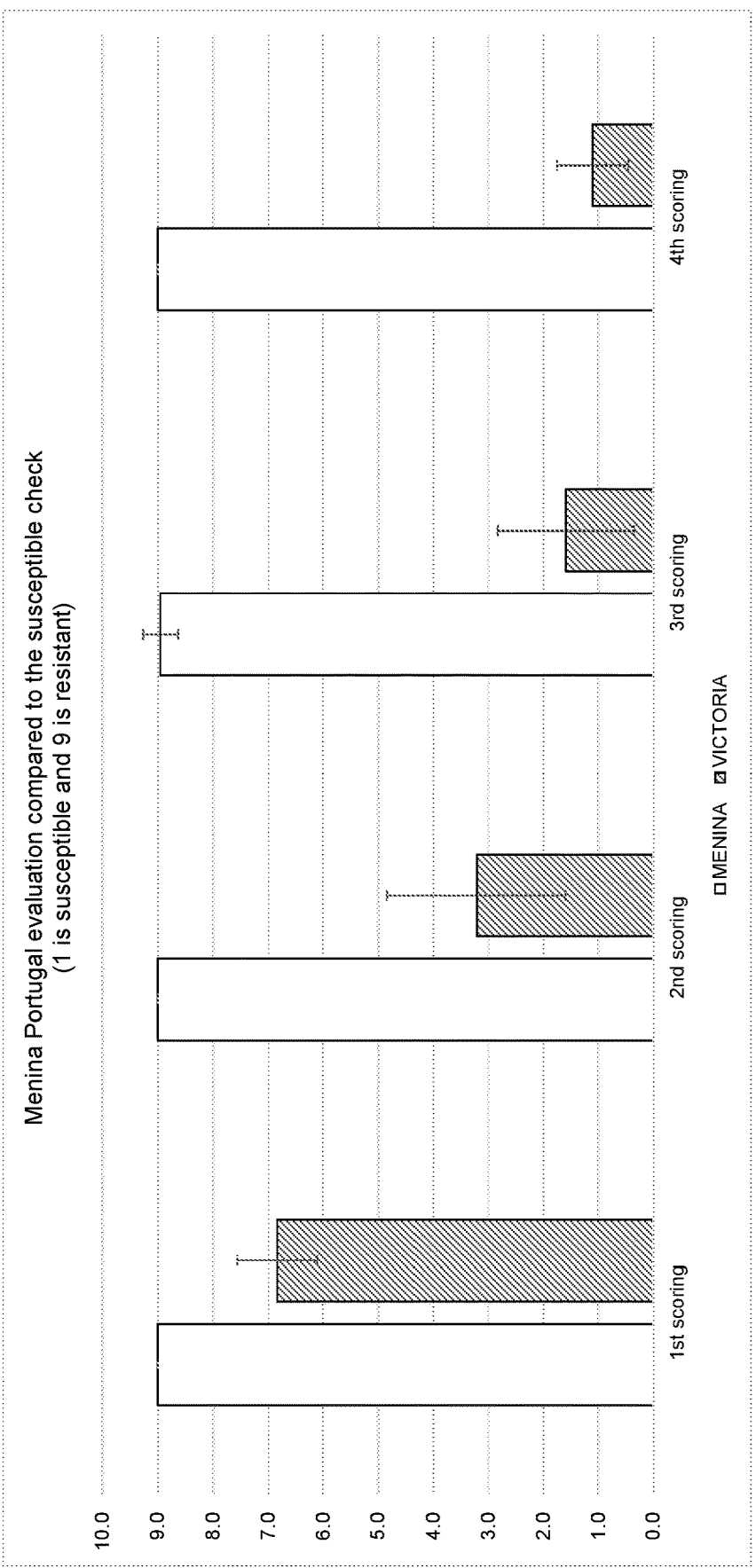
Figure 2. Evaluation of the resistance of *C. moschata* Menina Portugal accession in comparison to the susceptible check variety Victoria.

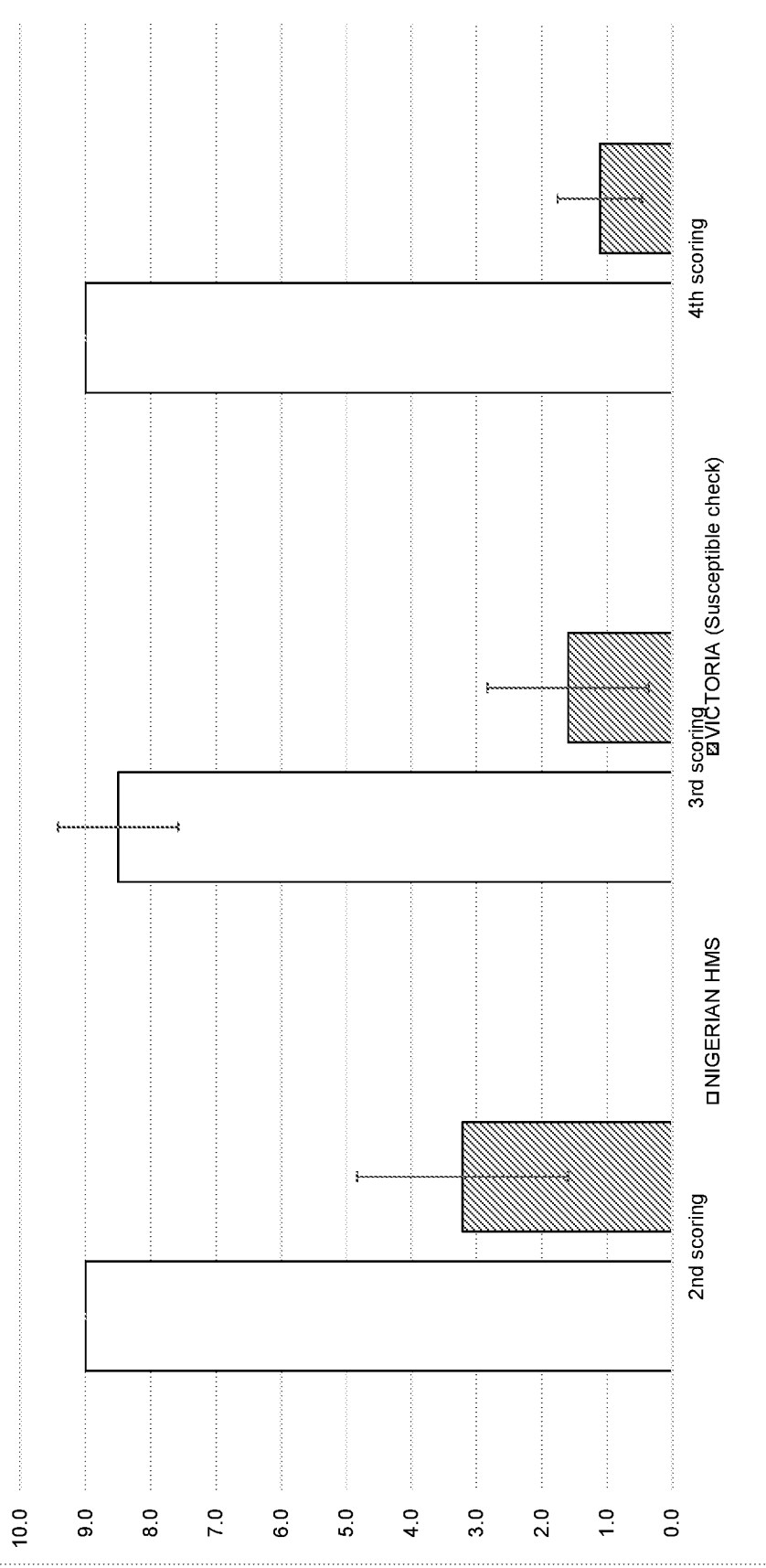
Figure 3. Evaluation of the resistance of C. *moschata* Nigerian accession in comparison to the susceptible check variety Victoria.

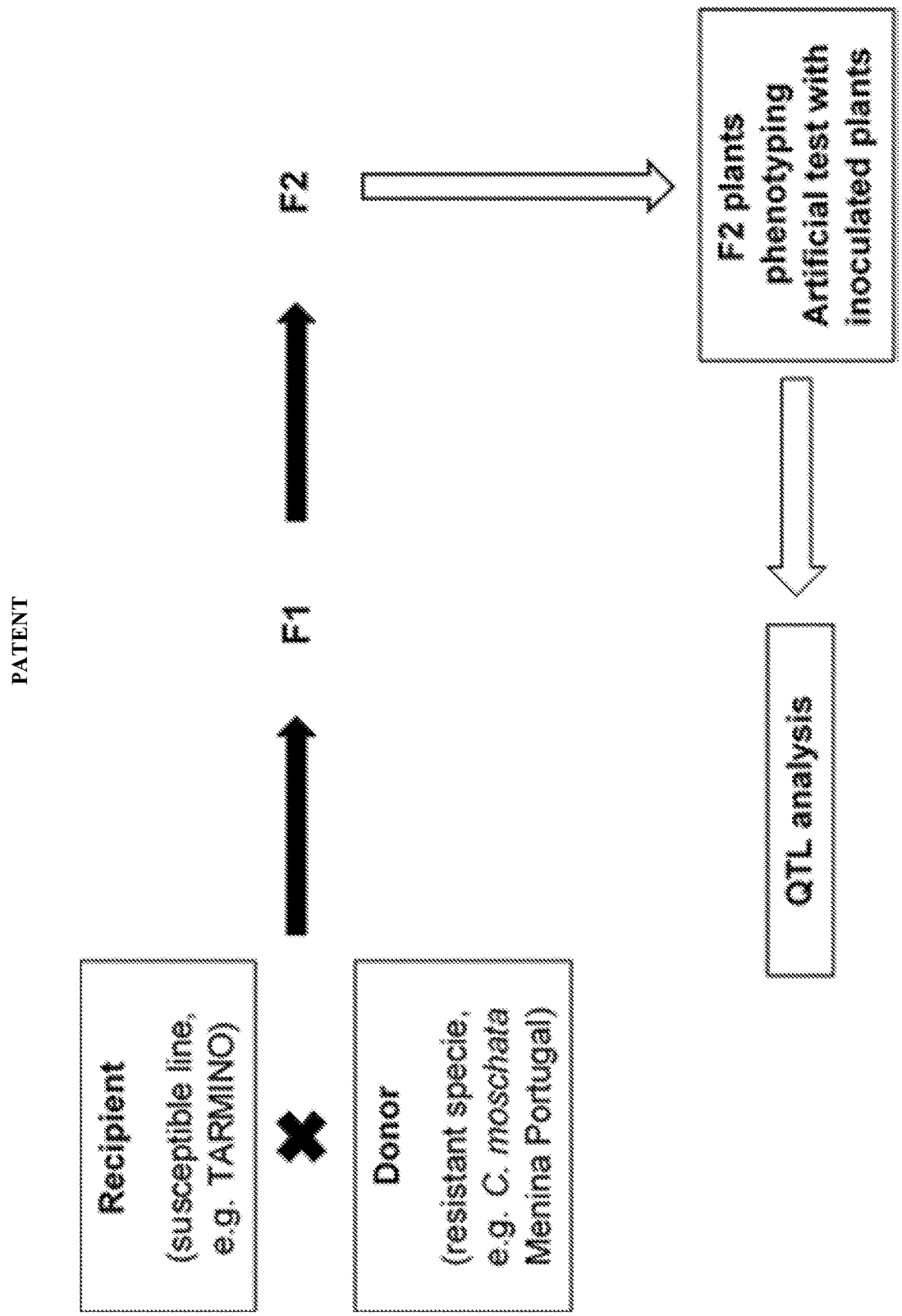
Figure 4. Exemplary scheme of the Advanced Backcross QTL mapping strategy.

|  |  | Year 1 | | Year 2 | | Year 3 | | Year 4 | |
| --- | --- | --- | --- | --- | --- | --- | --- | --- | --- |
|  |  | Cycle 1 | Cycle 2 | Cycle 3 | Cycle 4 | Cycle 5 | Cycle 6 | Cycle 7 | Cycle 8 |
| Without markers, only patho test | Survivor Test : BC resistant plant | BC0I1 → BC1I0 |  | BC1I1 →BC2I0 |  | BC2I1 →BC3I0 |  | BC3I1 →BC3I2 | BC3I2 →BC3I3 |
|  | Selfing |  | BC0I0 →BC1I1 |  | BC2I0 →BC2I1 |  | BC3I0 →BC3I1 |  |  |
| With marker | BC based on markers results | BC0I1 → BC1I0 | BC1I0 →BC2I0 | BC2I0 →BC3I0 |  |  |  |  |  |
|  | Selfing |  |  |  | BC3I0 →BC3I1 | BC3I1 →BC3I2 | BC3I2 →BC3I3 |  |  |

Figure 5. Breeding scheme of creating improved elite squash line resistant to ToLCNDV.

RESISTANCE TO TOLCNDV IN SQUASH

CROSS-REFERENCE TO RELATED APPLICATIONS

The present application is a national stage of International Patent Application Serial No. PCT/EP2016/077352, filed on Nov. 10, 2016, which claims priority to, and the benefit of U.S. Provisional Patent Application No. 62/253,427, filed Nov. 10, 2015, each of which is hereby incorporated by reference in its entirety for all purposes.

TECHNICAL FIELD

The application relates to plant breeding, plant pathology and molecular biology. In some embodiments, the application relates to identification of plants of the genus *Cucurbita*, such as *Cucurbita moschata* (*C. moschata*) plants, with tolerance or resistance to Tomato Leaf Curl New Dehli Virus (ToLCNDV), methods of developing plants of the genus *Cucurbita* (e.g., through plant breeding) with tolerance or resistance to said virus; and to the tolerant or resistant plants of the genus *Cucurbita* developed by such methods, and more particularly to *Cucurbita pepo* (*C. pepo*) plants tolerant or resistant to ToLCNDV.

BACKGROUND

The cucurbit family includes a number of valuable crop species (melon, cucumber, squash/pumpkin, watermelon). Production of cucurbit crops in large quantities is important worldwide, since cucurbits are important commercially in many regions, and are increasingly available throughout the year. According to Food and Agriculture Organization (FAO, 2002), world production of watermelon exceeded 80 million tons worldwide; cucumber exceeded 36 million tons; melon exceeded 22 million tons, and squash exceeded 17 million tons. However, a wide range of pathogens (virus, fungi, bacteria, nematodes, and insects) affects productivity of cucurbits (Blanchard et al., 1994, A color atlas of cucurbit diseases, New York: Manson Publishing/John Wiley; Zitter et al., 1996 Compendium of cucurbit diseases. St Paul, Minn.: APS Press). Among these, virus diseases of cucurbits are an important limitation in production. Massive damage up to total loss can be caused by virus, which prevents the growth of some cucurbit crops in certain area. Cucurbits are susceptible to many viruses from several virus families and virus resistance is therefore of major agricultural importance (Provvidenti, 1993, Resistance to viral disease of cucurbits. In: Kyle, M. M., ed. Resistance to viral diseases of vegetables. Portland, Oreg.: Timber Press; 1993:8-43).

The taxonomic family Geminiviridae includes some of the most important plant viruses causing severe diseases in agricultural, ornamental and horticultural crops. Transmission of these viruses can be via leafhoppers (mastreviruses, curtoviruses) or via species of whitefly (begomoviruses) or via treehoppers (topocuviruses).

The geminiviruses are responsible for a significant amount of crop damage worldwide. Diseases caused by these viruses have long been recognized as a limitation to the cultivation of several important crops, including maize, cassava, bean, squash, cucurbits, and tomato. Epidemics of geminivirus diseases have arisen due to a number of factors, including the recombination of different geminiviruses co-infecting a plant, which enables novel, possibly virulent viruses to be developed. Other contributing factors include the transport of infected plant material to new locations, expansion of agriculture into new growing areas, and the expansion and migration of vectors that can spread the virus from one plant to another.

Geminiviruses comprise a large and diverse family of viruses that infect a wide range of important monocotyledonous and dicotyledonous crop species and cause significant yield losses. Geminiviruses are classified into four genera: genus Mastrevirus (e.g., Maize streak virus), genus Curtovirus (e.g., Beet curly top virus), genus Begomovirus (e.g., SLCV), and genus Topocuvirus (Tomato pseudo-curly top virus).

The genus Begomovirus contains more than 200 viral species (Fauquet et al., 2008, Archives of Virology, 153(4): 783-821). They are plant viruses that as a group have a very wide host range. Natural hosts of begomoviruses are plant species in which the virus can replicate, cause systemic infection, and encapsidate, and from which virions are ingested and transmitted to a susceptible host by the whitefly vector (Funayama, 2001). Worldwide they are responsible for a large amount of economic damage to many important agronomic and horticultural crops such as tomatoes, beans, squash, cucurbits, cassava and cotton in subtropical and tropical regions of Americas, Africa and Asia. Begomoviruses cause stunting of plants, curling and yellowing of the leaves and low yield of fruits (Saeed et al., 2007, Journal of General Virology, 88:2881-2889). Morphologically, begomovirus particles are non-enveloped. The nucleocapsid is 38 nm long and 15-22 nm in diameter. While particles have basic isocahedral symmetry, they consist of two incomplete icosahedra—missing one vertex—joined together. There are 22 capsomeres per nucleocapsid. Begomovirus species has single stranded closed circular DNA. Most begomoviruses have a bipartite genome, meaning that the genome is segmented into two segments (referred to as DNA A and DNA B) that are packaged into separate particles. Both segments are generally required for successful symptomatic infection in a host cell, but DNA B is dependent for its replication upon DNA A, which can in some begomoviruses apparently cause infections on its own.

Tomato leaf curl New Delhi virus (ToLCNDV), a begomovirus, can cause severe losses in many crops. It was first described on tomatoes in India in 1995, but subsequently, many reports of damages to cucurbit crops have also been made, first in other Asian countries and more recently in Europe: in September 2012, symptoms have been observed on squash in Spain, first in Murcia region, then, by May 2013 in Almeria province, not anymore in squash but also on melon and pumpkins. Symptoms included curling and severe mosaic of the young leaves, very short internodes, fruit skin roughness and longitudinal cracking of the fruits, leading to catastrophic losses.

Current methods of preventing and controlling geminiviruses include controlling the spread of insect vectors that carry the virus, developing transgenic plants expressing the viral coat protein, and using classical breeding methods to develop plants having natural resistance to the virus. Disease resistant plants developed using classical plant breeding offer an effective, safe, and relatively less expensive method of controlling many crop diseases.

Islam et al., 2011, J. Hort. Sci & Biotechnol., 86:661-667 reported a monogenic dominant resistance in a breeding line of sponge gourd (*Luffa cylindrica* M. Roem). Lopez et al., 2015, Euphytica, 204(3):679-691 conducted the first published screenings of cucurbit germplasm for the identification of tolerance sources. In general, *C. pepo* accessions are highly susceptible to the virus, whereas *C. maxima* and *C. moschata* accessions showed mild to severe symptoms. This suggests that identifying resistant *Cucurbita* plants is highly difficult, and explain why there is still no commercial cultivar of the genus *Cucurbita* available on the market.

Therefore, there is an important need in the art to identify a reliable source of resistance and/or tolerance which could then be used to obtain tolerant or resistant commercial plants of the genus *Cucurbita*, and more particularly to obtain tolerant or resistant *C. pepo* plants.

SUMMARY

The present inventors have identified wild *C. moschata* plants which display a high level of resistance to ToLCNDV and they have been able to introgress, into *C. pepo* genetic background, the *C. moschata* sequences (i.e. quantitative trait loci (QTLs)) conferring resistance or tolerance to ToLCNDV, thus obtaining resistant or tolerant *C. pepo* plants.

The present invention thus provides a *C. pepo* plant tolerant or resistant to ToLCNDV, wherein said plant comprises a QTL associated with tolerance or resistance to ToLCNDV on linkage group 11 (LG11). In some embodiments, said QTL on LG11 is genetically linked to the markers SQ-0006678 (SEQ ID NO: 8), SQ-0010844 (SEQ ID NO: 9) and/or SQ-0000209 (SEQ ID NO: 10). In some embodiments, said QTL on LG11 is located in a locus encompassing the markers SQ-0006678 (SEQ ID NO: 8), SQ-0010844 (SEQ ID NO: 9) and/or SQ-0000209 (SEQ ID NO: 10). In some embodiments, said QTL on LG11 is located within a chromosomal region delimited by marker SQ-0006678 (SEQ ID NO: 8) and marker SQ-0000209 (SEQ ID NO: 10). In some embodiments, said QTL on LG11 is located within a chromosomal region delimited by marker SQ-0010844 (SEQ ID NO: 9) and marker SQ-0000209 (SEQ ID NO: 10). These markers have predictive value for the phenotype of interest, i.e. the tolerance or resistance to ToLCNDV.

In some embodiments, said QTL associated to tolerance or resistance to ToLCNDV is chosen from those present in the genome of the plant TLG, a representative sample of seed of which has been deposited under NCIMB number 42686.

In some embodiments, said QTL associated to tolerance or resistance to ToLCNDV is as found in the genome of the plant TLG, a representative sample of seed of which has been deposited under NCIMB number 42686.

Also provided is a cell of the *Cucurbita pepo* (*C. pepo*) plant according to the invention. The cell comprises the QTL associated to tolerance or resistance to ToLCNDV.

Further provided is a plant part obtained from a *Cucurbita pepo* (*C. pepo*) plant according to the invention. In some embodiments, said plant part is a seed, a fruit, a reproductive material, roots, flowers, a rootstock or a scion. The plant part comprises the QTL associated to tolerance or resistance to ToLCNDV.

The present invention also provides a seed of a *Cucurbita pepo* (*C. pepo*) plant, giving rise when grown up to a *C. pepo* plant according to the invention. The seed comprises the QTL associated to tolerance or resistance to ToLCNDV.

The present invention also provides methods for diagnosing a plant of the genus *Cucurbita* for ToLCNDV. In one embodiment, the methods comprise detecting the presence of any proteins derived from ToLCNDV, based on immunological detection. In another embodiment, said ToLCNDV protein is one or more ToLCNDV proteins as described elsewhere herein. In another embodiment, the methods comprise detecting the presence of one or more ToLCNDV-specific nucleic acid sequences corresponding to the one or more isolated ToLCNDV nucleic acid sequences as described elsewhere herein, based on nucleotide hybridization or amplification.

In one embodiment, the methods comprise: a) contacting a biological sample with one or more antibodies as described elsewhere herein, under conditions for antibody binding. In one embodiment, the methods further comprise b) detecting presence or absence of the binding. In one embodiment, said biological sample is a plant extract. In one embodiment, the detecting step comprises an immunological detection test. In some embodiments, the immunological detection test is selected from the group consisting of precipitation and agglutination tests, immunogold labeling, immunosorbent electron microscopy, enzyme linked immunosorbent assay (ELISA), Western blot, radioimmunoassay (RIA), and dot blot. In one embodiment, the ELISA is a direct antibody sandwich enzyme linked immunosorbent assay (DAS-ELISA). In another embodiment, the ELISA is a Lateral Flow test. In another embodiment, the ELISA is a triple antibody sandwich enzyme linked immunosorbent assay (TAS-ELISA).

In another embodiment, the methods comprise a) extracting nucleic acids from a biological sample and b) detecting the presence or absence of one or more ToLCNDV-specific nucleic acids. In one embodiment, the ToLCNDV-specific nucleic acid sequences are in one or more different regions. In one embodiment, said regions can be of one or more different genes of a ToLCNDV. In one embodiment, the biological sample can be prepared by any method, wherein the sample contains a template selected from the group consisting of DNA, RNA, and otherwise, so long as the template fits the criteria for amplification purposes by those skilled in the art. In one embodiment, said amplification method is PCR. In one embodiment, said amplification method is RT-PCR. In one embodiment, the RT-PCR is performed using a real time PCR technique. In another embodiment, the detecting step comprises nucleic acid hybridization between the ToLCNDV-specific nucleic acid and one or more ToLCNDV-specific probes. In one embodiment, said nucleic acid hybridization is a Northern blot or a Southern blot.

The present invention also provides methods of screening a plant population, plant, plant part, plant tissue, and/or plant cell of the genus *Cucurbita* that is tolerant/resistant or susceptible to ToLCNDV, comprising: a) growing the plant population, plant, plant part, plant tissue, or plant cell; In one embodiment, the methods further comprise b) challenging the plant population, plant, plant part, plant tissue, plant cell of the genus *Cucurbita* with the isolated ToLCNDV strain as described elsewhere herein; In one embodiment, the methods further comprise c) evaluating the tolerance or resistance in the plant population, plant, plant part, plant tissue, plant cell of the genus *Cucurbita*, wherein a plant population, plant, plant tissue, plant cell of the genus *Cucurbita* that is tolerant/resistant or susceptible to ToLCNDV is identified. In one embodiment, the methods further comprise d) detecting the presence of a QTL associated to tolerance or resistance to ToLCNDV in the plant population, plant, plant part, plant tissue, plant cell of the genus *Cucurbita*, as indicated by the presence of one or more of the markers selected from the group consisting of SQ-0006678 (SEQ ID NO: 8), SQ-0010844 (SEQ ID NO: 9), SQ-0000209 (SEQ ID NO: 10), and any other markers within a chromosomal region delimited by marker SQ-0006678 (SEQ ID NO: 8) and marker SQ-0000209 (SEQ ID NO: 10), or a chromosomal region delimited by marker SQ-0010844 (SEQ ID NO: 9)

and marker SQ-0000209 (SEQ ID NO: 10), such as by the presence of the marker SQ-0010844 (SEQ ID NO: 9) and/or marker SQ-0000209 (SEQ ID NO: 10).

In some embodiment, said plant of the genus *Cucurbita* is a *Cucurbita pepo* (*C. pepo*), *Cucurbita moschata* (*C. moschata*), *Cucurbita okeechobeensis* (*C. okeechobeensis*), *Cucurbita pedatifolia* (*C. pedatifolia*) or a *Cucurbita maxima* (*C. maxima*) plant. In some embodiments, the *C. moschata* plant is 'Nigerian', 'Menina Portugal', 'Menina Brasileira', or hybrid thereof.

In one embodiment, said evaluating step comprises visual estimation. In one embodiment, said evaluating step comprising a molecular test or a biological test of virus density. In one embodiment, said visual observation comprises a resistance or tolerance scoring system. In one embodiment, said molecular test comprises evaluating the density of ToLCNDV-specific nucleic acids corresponding to any nucleic acid sequences as described above, or the density of ToLCNDV-specific amino acids as described above. In one embodiment, said density of ToLCNDV-specific nucleic acids is evaluated by molecular method comprising nucleic acids test. In some embodiments, the nucleic acid test is selected from the group consisting of PCR, RT-PCR, Northern blot and Southern blot. In one embodiment, said molecular method comprises testing the density of ToLCNDV protein corresponding to any amino acid sequences as described above. In one embodiment, said method is performed in an ELISA (e.g., Lateral Flow test, or DAS-ELISA, or TAS-ELISA), Western blot, RIA, or dot blot. In one embodiment, said density of ToLCNDV-specific amino acids is evaluated by molecular method comprising an immunological detection test selected from the group consisting of precipitation and agglutination tests, immunogod labeling, immunosorbent electron microscopy, enzyme linked immunosorbent assay (ELISA, e.g., Lateral Flow test, or DAS-ELISA, or TAS-ELISA), Western blot, radioimmunoassay (RIA), and dot blot. The present invention also provides a plant population, plant part, plant, plant tissue or plant cell population, plant, plant part, plant tissue, and/or plant cell of the genus *Cucurbita* wherein the plant population, plant, plant part, plant tissue or plant cell of the genus *Cucurbita* is resistant or tolerant to ToLCNDV. In some embodiment, said plant of the genus *Cucurbita* is a *Cucurbita pepo* (*C. pepo*), *Cucurbita moschata* (*C. moschata*), *Cucurbita okeechobeensis* (*C. okeechobeensis*), *Cucurbita pedatifolia* (*C. pedatifolia*) or a *Cucurbita maxima* (*C. maxima*) plant.

The present invention also provides a tissue culture of the plant population, plant, plant part, plant tissue or plant cell of the genus *Cucurbita*, wherein said tissue culture retains resistance or tolerance to ToLCNDV.

The present invention also provides a seed derived from the plant population, plant, plant part, plant tissue or plant cell of the genus *Cucurbita*, wherein said seed can give rise to a plant of the genus *Cucurbita* that is also resistant or tolerant to ToLCNDV.

The present invention also provides a progeny derived from the plant of the genus *Cucurbita* as described above, whether produced sexually or asexually, wherein said progeny retains resistance or tolerance to ToLCNDV.

The present invention also provides a method of identifying and/or isolating a nucleic acid sequence conferring resistance or tolerance to ToLCNDV, comprising: a) crossing a plant of the genus *Cucurbita* resistant or tolerant to ToLCNDV as a donor with a suitable plant of the genus *Cucurbita* that is susceptible to said virus to produce offspring plants as a mapping population; In some embodiments, the method further comprises b) challenging said offspring plants with said virus and determining the tolerance or resistance in said offspring plants; In some embodiments, the method further comprises c) cloning the nucleic acid. In one embodiment, said cloning step comprises map-based cloning. In another embodiment, said cloning step comprises association mapping.

The present invention also provides a method of identifying one or more quantitative trait locus (QTL) contributing to the resistance or tolerance to the isolated virus of present invention, comprising: a) crossing the plant of the genus *Cucurbita* resistant or tolerant to ToLCNDV as a donor with a suitable plant of the genus *Cucurbita* that is susceptible to said virus to produce offspring plants; In some embodiments, the method further comprises b) challenging one or more said offspring plants with an infective dosage of said virus; In some embodiments, the method further comprises c) quantitatively determining the resistance or tolerance in said one or more offspring plants; In some embodiments, the method further comprises d) establishing a genetic linkage map that links the observed resistance or tolerance to the presence of chromosomal markers of said donor plant in said one or more offspring plants; In some embodiments, the method further comprises e) assigning to a QTL the contiguous markers on said map that are linked to enhanced disease resistance or tolerance.

The present invention also provides a plant population, plant, plant part, plant tissue, or plant cell of the genus *Cucurbita* that is tolerant or resistant to ToLCNDV, wherein the plant population, plant, plant part, plant tissue, or plant cell of the genus *Cucurbita* is produced by transferring a nucleic acid sequence conferring resistance or tolerance to ToLCNDV, and/or one or more QTLs contributing to the resistance or tolerance isolated by the methods described above, to a plant population, plant, plant part, plant tissue, or plant cell of the genus *Cucurbita*. In one embodiment, the nucleic acid sequence and/or the QTLs can be transferred by breeding methods. In one embodiment, said breeding method comprises using introgression line library. In another embodiment, the nucleic acid sequence and/or the QTLs can be transferred by plant transformation.

The present invention further provides methods of breeding plants of the genus *Cucurbita* that are tolerant or resistant to Tomato leaf curl New Delhi virus (ToLCNDV). In some embodiments, the methods comprise (i) providing a first plant of the genus *Cucurbita*, said first plant of the genus *Cucurbita* being tolerant or resistant to ToLCNDV; In some embodiments, the methods further comprise (ii) crossing said first plant of the genus *Cucurbita* provided in step (i) with a second plant to produce progeny plants of a subsequent generation. In some embodiments, the second plant is a plant of the genus *Cucurbita*. In some embodiments, the methods further comprise (iii) selecting one or more progeny plants that contain the tolerance or resistance to ToLCNDV from the progeny of the subsequent generation; In some embodiments, the methods further comprise (iv) backcrossing the selected progeny plants that contain the tolerance or resistance to ToLCNDV or selfed offspring thereof with a second plant of the genus *Cucurbita* to produce backcross progeny plants; In some embodiments, the methods further comprise (v) selecting for backcross progeny plants that contain the tolerance or resistance to ToLCNDV from the backcross progeny plants; In some embodiments, the methods further comprise (vi) repeating steps (iv) and (v) three, four, five, six, seven or more times in succession to produce selected fourth or higher backcross progeny plants that are tolerant or resistant to ToLCNDV. In some embodiments, the progeny plants selected in steps (iv) to (vi) are optionally selected by detecting the presence of a QTL associated to tolerance or resistance to ToLCNDV as indicated by the presence of one or more of the markers selected from the group consisting of SQ-0006678 (SEQ ID NO: 8), SQ-0010844 (SEQ ID NO: 9), SQ-0000209 (SEQ ID NO: 10), and any other markers within a chromosomal region delimited by marker SQ-0006678 (SEQ ID NO: 8) and marker SQ-0000209 (SEQ ID NO: 10), or a chromosomal region delimited by marker SQ-0010844 (SEQ ID NO: 9) and marker SQ-0000209 (SEQ ID NO: 10), such as by the presence of the marker SQ-0010844 (SEQ ID NO: 9) and/or marker SQ-0000209 (SEQ ID NO: 10).

In some embodiments, the first plant of the genus *Cucurbita* resistant or tolerant to ToLCNDV is *Cucurbita pepo* (*C. pepo*), *Cucurbita moschata* (*C. moschata*), *Cucurbita okeechobeensis* (*C. okeechobeensis*), *Cucurbita pedatifolia* (*C. pedatifolia*) or a *Cucurbita maxima* (*C. maxima*) plant. In some embodiments, the first plant of the genus *Cucurbita* tolerant or resistant to ToLCNDV is a *C. moschata* plant or a *C. pedatifolia* plant. In some embodiments, the *C. moschata* plant tolerant or resistant to ToLCNDV is 'Nigerian', 'Menina Portugal', 'Menina Brasileira', or hybrid thereof.

In some embodiments, the second plant of the genus *Cucurbita* is a plant having desired trait and physiological and morphological characteristics. In some embodiments, said second plant of the genus *Cucurbita* is a *C. pepo* plant having desired trait and physiological and morphological characteristics For example, the second plant of the genus *Cucurbita* is a commercial elite plant second plant of the genus *Cucurbita*, e.g. a *C. pepo* plant, that is susceptible to ToLCNDV.

In some embodiments, the second plant of the genus *Cucurbita* is a *Cucurbita pepo* plant. For example, the second plant of the genus *Cucurbita* is KAZA121, FES, KARIBA, TARMINO, VICTORIA, GLORIA, CORA, SINATRA, MUSA, LOREA, ASMA, JEDIDA, FALALI, VIGNE, or hybrid thereof.

Accordingly, the present invention provides plants of the genus *Cucurbita* produced by the breeding methods described above. In some further embodiments, the present invention provides a plant, plant part, or plant cell of the genus *Cucurbita* derived from the plant of the genus *Cucurbita* produced by the breeding methods described above, for example, plant seeds of the genus *Cucurbita* derived from said selected plant of the genus *Cucurbita*.

The present invention also provides methods of breeding squash tolerant or resistant to Tomato Leaf Curl New Dehli Virus (ToLCNDV), wherein the method comprises (i) providing a first squash plant, said first squash plant being tolerant or resistant to ToLCNDV; In some embodiments, the methods further comprise (ii) crossing the squash plant provided in step (i) with a second squash plant to produce progeny plants of the subsequent generation; In some embodiments, the methods further comprise (iii) selecting one or more progeny plants that contain the tolerance or resistance to ToLCNDV from the progeny of the subsequent generation; In some embodiments, the methods further comprise (iv) backcrossing the selected progeny plants that contain the tolerance or resistance to ToLCNDV or selfed offspring thereof with the second squash plant to produce backcross progeny plants; In some embodiments, the methods further comprise (v) selecting for backcross progeny plants that contain the tolerance or resistance to ToLCNDV from the backcross progeny plants; In some embodiments, the methods further comprise (vi) repeating steps (iv) and (v) three, four, five, six, seven or more times in succession to produce selected fourth or higher backcross progeny plants that are tolerant or resistant to ToLCNDV. In some embodiments, the progeny plants selected in steps (iv) to (vi) are optionally selected by detecting the presence of a QTL associated to tolerance or resistance to ToLCNDV as indicated by the presence of one or more of the markers selected from the group consisting of SQ-0006678 (SEQ ID NO: 8), SQ-0010844 (SEQ ID NO: 9), SQ-0000209 (SEQ ID NO: 10), and any other markers within a chromosomal region delimited by marker SQ-0006678 (SEQ ID NO: 8) and marker SQ-0000209 (SEQ ID NO: 10), or a chromosomal region delimited by marker SQ-0010844 (SEQ ID NO: 9) and marker SQ-0000209 (SEQ ID NO: 10), such as by the presence of the marker SQ-0010844 (SEQ ID NO: 9) and/or marker SQ-0000209 (SEQ ID NO: 10).

Accordingly, the present invention provides squash plants produced by the breeding methods described above. In some further embodiments, the present invention provides a squash plant, plant part, or plant cell derived from the plant produced by the breeding methods described above, for example, squash plant seeds derived from said selected plant.

The invention also provides the use of the plant according to the invention as a breeding partner in a breeding program for obtaining *C. pepo* plant tolerant or resistant to ToLCNDV.

BRIEF DESCRIPTION OF THE DRAWINGS

FIG. 1 depicts the percentage of plants infected by ToLCNDV among four replications for 29 accessions tested.

FIG. 2 depicts the evaluation of the resistance of *C. moschata* Menina Portugal accession to ToLCNDV in comparison to the susceptible check variety Victoria.

FIG. 3 depicts the evaluation of the resistance of *C. moschata* Nigerian accession to ToLCNDV in comparison to the susceptible check variety Victoria.

FIG. 4 depicts the exemplary scheme of the Advanced Backcross QTL mapping strategy.

FIG. 5 depicts the breeding scheme of creating improved elite squash line resistant to ToLCNDV.

BRIEF DESCRIPTION OF THE SEQUENCE LISTING

SEQ ID NO: 1 corresponds to the genomic sequence of the ToLCNDV virus referenced under NCBI Reference Number KF749223.1.

SEQ ID NO: 2 corresponds to the genomic sequence of the ToLCNDV virus referenced under NCBI Reference Number KF749225.1.

SEQ ID NO: 3 shows the sequence of a suitable nucleic acid genome fragment for identifying the ToLCNDV.

SEQ ID NO: 4 and 5 show the sequence of the primers for detecting Begomoviruses.

SEQ ID NO: 6 and 7 show the sequence of the primers for detecting the ToLCNDV.

SEQ ID NO: 8 shows the flanking sequences of the marker SQ-0006678.

SEQ ID NO: 9 shows the flanking sequences of the marker SQ-0010844.

SEQ ID NO: 10 shows the flanking sequences of the marker SQ-0000209.

DESCRIPTION OF THE TEXT FILE SUBMITTED ELECTRONICALLY

The contents of the text file submitted electronically herewith are incorporated herein by reference in their entireties: A computer readable format copy of the Sequence Listing (filename: VILM_018_01WO_SeqList.txt, date recorded: Nov. 9, 2016, file size 12 kilobytes).

DETAILED DESCRIPTION

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

DEFINITIONS

As used herein, the verb "comprise" as is used in this description and in the claims and its conjugations are used in its non-limiting sense to mean that items following the word are included, but items not specifically mentioned are not excluded.

As used herein, the term "plant of the genus Curcurbita" refers to any plant belonging to the genus Cucurbita. In some embodiment, said plant of the genus Cucurbita is a Cucurbita pepo (C. pepo), Cucurbita moschata (C. moschata), Cucurbita okeechobeensis (C. okeechobeensis), Cucurbita pedatifolia (C. pedatifolia) or a Cucurbita maxima (C. maxima) plant. In some embodiments, the C. moschata plant is 'Nigerian', 'Menina Portugal', 'Menina Brasileira', or hybrid thereof.

As used herein, the term "plant part" refers to any part of a plant including but not limited to the shoot, root, rootstock, scion, stem, seeds, stipules, leaves, petals, flowers, ovules, bracts, branches, petioles, internodes, bark, pubescence, tillers, rhizomes, fronds, blades, pollen, stamen, fruit, and the like. The two main parts of plants grown in some sort of media, such as soil, are often referred to as the "aboveground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "chimeric protein" refers a constructs that links at least two heterologous proteins into a single macromolecule (fusion protein).

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "homologous" or "homologue" or "ortholog" is known in the art and refers to related sequences that share a common ancestor or family member and are determined based on the degree of sequence identity. The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. In some embodiments, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations containing alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "agent", as used herein, means a biological or chemical compound such as a simple or complex organic or inorganic molecule, a peptide, a protein or an oligonucleotide that modulates the function of a nucleic acid or polypeptide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

As used herein, the term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "substantially complementary" means that two nucleic acid sequences have at least about 65%, about 70% or 75%, about 80% or 85%, about 90% or 95%, or about 98% or 99%, sequence complementarities to each other. This means that primers and probes must exhibit sufficient complementarity to their template and target nucleic acid, respectively, to hybridize under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

As used herein, the term "isolated virus" refers to a whole virus or a fragment of a virus which is obtained from any source whatsoever (e.g., from soil, from an insect, from a plant, or from part of a plant) through a method selected from the group consisting of physical, chemical, and/or biological separation/transfection methods, which includes, but are not limited to grinding, squeezing, smashing, cutting, soaking, washing, centrifuging, gradient centrifuging, ultra-centrifuging, thin layer centrifuging, chromatography, electrophoresis, electro-extraction, immunoprecipitation, inoculation, transfection, et al. The isolated virus can be in a liquid form, a solid form, or a mixture thereof. For example, said isolated virus is directly obtained by grinding plant leaf tissue and collecting the grinded material. An isolated virus can be used in the following exemplary infection procedures: 1) growing a healthy scion on a virus-infected rootstock, or vice versa; 2) exposing a healthy plant to transmission vectors containing the virus; 3) introducing into a healthy plant an expression vector harboring a coding region of the virus genome; 4) use of agro-infectious clones, such as *Agrobacterium tumefaciens* strains containing an expression vector harboring a coding region of the virus genome. Thus, in the context of the present invention, methods for challenging a plant, plant part, and/or plant cell to an infective dosage of ToLCNDV are not limited to any particular method. For example, infection may comprise mechanical inoculation of the virus on healthy plants. In one embodiment, a portion of a diseased leaf may be rubbed directly onto a leaf of a plant that is to be challenged.

As used herein, the term "substantially pure virus" refers to a whole virus or a fragment or a particle of a virus which is obtained from any source whatsoever wherein the virus or virus fragment or particle is substantially separated from other components which may accompany it and/or are naturally associated with it. Thus, a substantially pure virus may be one wherein the composition comprising the virus also contains minor amounts of other substances, also known as impurities, such as small amounts of plant tissue or soil minerals. Generally, a virus or virus fragment or particle is considered to be substantially pure if it contains less than about 5% of other materials, or if it contains less than about 4% of other materials, or if it contains less than about 3% of other materials, or if it contains less than about 2% of other materials, or if it contains less than about 1% of other materials, or if it contains less than about 0.5% of other materials.

As used herein, the term "suppression" or "disruption" of regulation refers to reduced activity of regulatory proteins, and such reduced activity can be achieved by a variety of mechanisms including antisense, mutation knockout or RNAi. Antisense RNA will reduce the level of expressed protein resulting in reduced protein activity as compared to wild type activity levels. A mutation in the gene encoding a protein may reduce the level of expressed protein and/or interfere with the function of expressed protein to cause reduced protein activity.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer can be single stranded for maximum efficiency in amplification. In some embodiments, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001.

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, the term "recombinant" refers to an artificial combination of two otherwise separated segments of sequence, e.g., by chemical synthesis or by the manipulation of isolated segments of nucleic acids by genetic engineering techniques.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., 1985, EMBO J. 4:2411-2418; De Almeida et al., 1989, Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. The term "expression", as used herein, refers to the production of a functional end-product e.g., an mRNA or a protein (precursor or mature).

As used herein, the phrase "plant-expressible selectable or screenable marker" refers to a genetic marker functional in a plant cell. A selectable marker (e.g. a kanamycin resistance gene) allows cells containing and expressing that marker to grow under conditions unfavorable to growth of cells not expressing that marker. A screenable marker (e.g. a beta-galactosidase gene) facilitates identification of cells which express that marker.

As used herein, the term "inbred", "inbred plant" is used in the context of the present invention, this also includes any single gene conversions of that inbred. The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "infective dosage" is defined as a dosage of viral particles or virus nucleic acid capable of infecting a plant, which dosage may vary between plants and between viruses tested. Infection in this way may be achieved by mechanical inoculation of purified virus particles or virus nucleic acid on plants.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced from that of uninfected plants. As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of a plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under nominal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance is well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 5 being the resistance score applied to the most resistant plants (e.g., no symptoms, or with the least symptoms), and 1 the score applied to the plants with the most severe symptoms, then a line is rated as being resistant when at least 75% of the plants have a resistance score at a 3, 4, or 5 level, while susceptible lines are those having more than 25% of the plants scoring at a 1 or 2 level. If a more detailed visual evaluation is possible, then one can use a scale from 1 to 10 so as to broaden out the range of scores and thereby hopefully provide a greater scoring spread among the plants being evaluated. Alternatively or in addition to such visual evaluations, the evaluation can also be performed by determining the virus bio-density in a plant or plant part through molecular biological methods, such as protein hybridization (e.g., ELISA, measuring viral protein density) and/or nucleic acid hybridization (e.g., RT-PCR, measuring viral RNA density). A plant is resistant to the virus strain if it has a virus RNA and/or protein density that is about 50%, about 40%, about 30%, about 20%, about 10%, about 5%, about 2%, about 1%, about 0.1%, about 0.01%, about 0.001%, or about 0.0001% of the RNA and/or protein density in a susceptible plant.

As used herein, the term "full resistance" is referred to as complete failure of the virus to develop after infection, and may either be the result of failure of the virus to enter the cell (no initial infection) or may be the result of failure of the virus to multiply in the cell and infect subsequent cells (no subliminal infection, no spread). The presence of full resistance may be determined by establishing the absence of viral particles or viral RNA in cells of the plant, as well as the absence of any disease symptoms in said plant, upon exposure of said plant to an infective dosage of virus (i.e. after 'infection'). Among breeders, this phenotype is often referred to as "immune". "Immunity" as used herein thus refers to a form of resistance characterized by absence of viral replication even when virus is actively transferred into cells by e.g. electroporation.

As used herein, the term "partial resistance" is referred to as reduced multiplication of the virus in the cell, as reduced (systemic) movement of the virus, and/or as reduced symptom development after infection. The presence of partial resistance may be determined by establishing the systemic presence of low titres of viral particles or viral RNA in the plant and the presence of decreased or delayed disease-symptoms in said plant upon exposure of said plant to an infective dosage of virus. Virus titres may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "hypersensitive" refers to a foam of resistance whereby the infection remains local and does not systemically spread, for instance due to local necrosis of infected tissue or lack of systemic movement beyond inoculated tissue. Hypersensitive plants show local, but severe disease symptoms and the local presence of the virus can be established in such plants.

As used herein, the term "tolerant" is used herein to indicate a phenotype of a plant wherein disease-symptoms remain absent upon exposure of said plant to an infective dosage of virus, whereby the presence of a systemic or local viral infection, virus multiplication, at least the presence of viral genomic sequences in cells of said plant and/or genomic integration thereof can be established. Tolerant plants are therefore resistant for symptom expression but symptomless carriers of the virus. Sometimes, viral sequences may be present or even multiply in plants without causing disease symptoms. This phenomenon is also known as "latent infection". Some DNA and RNA viruses, may become undetectable following a primary infection only to reappear later and produce acute disease. In latent infections, the virus may exist in a truly latent non-infectious occult form, possibly as an integrated genome or an episomal agent (so that viral particles cannot be found in the cytoplasm, while PCR protocols may indicate the present of viral nucleic acid sequences) or as an infectious and continuously replicating agent. A reactivated virus may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the virus resulting in entry of the virus into the plant's cells and multiplication and systemic spread of virus, resulting in disease symptoms. The term "susceptible" is therefore equivalent to "non-resistant". A susceptible plant exhibits normal virus titres in its cells upon infection. Susceptibility may thus be determined by establishing the presence of normal (i.e. relative to other viral infections in plants) titres of viral particles or of viral RNA in cells of the plant and the presence of normal disease symptoms in said plant upon exposure of said plant to an infective dosage of virus.

As used herein, the term "sensitive" reflects the symptomatic reaction of a susceptible plant upon virus infection. The reaction or symptoms can be more or less severe depending on the level of sensitivity of the plant. If the plant is injured or even killed by the virus, said plant is qualified as "sensitive".

As used herein the term "ToLCNDV-resistant," is to be interpreted as referring to the resistance of a plant, plant tissue, or plant cell of the genus *Cucurbita*, to the establishment of an infection, or the establishment of a disease caused by a the new virus as defined in the present invention, unless expressly stated or intended otherwise.

As used herein, the term "ToLCNDV-specific" as used herein refers to a nucleic acid sequence, or an amino acid sequence having a sequence that is specific for the genus of viruses comprising the virus as defined in the present invention. With the term "specific" is meant that the nucleic acid sequence or the amino acids sequence is capable of hybridizing specifically under stringent hybridization conditions to the nucleic acid of said virus, or to an antibody of a ToLCNDV-specific protein of the said virus.

As used herein, the term "sample" includes a sample from a plant, a plant part, a plant cell, or from a transmission vector, or a soil, water or air sample.

As used herein, the term "biological sample" includes a DNA sample, a RNA sample, and/or a protein sample extracted from any part of a plant (e.g. leaf, fruit, stem)

As used herein, the term "transmission vector" refers to the disease-spreading agent or substance.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, reference to the linkage group 11 (LG11) is made from the genetic map published by Esteras et al. (BMC Genomics 2012, 13:80, DOI: 10.1186/1471-2164-13-80).

As used herein, reference to the CP32_scaffold000045 is made from the CucurbiGene genome draft v3.2 (https://cucurbigene.upv.es/genome-v3.2/).

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus. As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the terms "genetically linked to" refers to the situation wherein the two genetic elements are segregating together over one or more generation. More specifically, by "a QTL associated to tolerance or resistance genetically linked to a marker", it is meant that the QTL associated to a tolerance or resistance is segregating with the marker over one or more generation. For example, the genetic distance between the QTL and the marker is about 4.9 cM, 4.8 cM, 4.7 cM, 4.6 cM, 4.5 cM, 4.4 cM, 4.3 cM, 4.2 cM, 4.1 cM, 4.0 cM, about 3.9 cM, 3.8 cM, 3.7 cM, 3.6 cM, 3.5 cM, 3.4 cM, 3.3 cM, 3.2 cM, 3.1 cM, 3.0 cM, about 2.9 cM, 2.8 cM, 2.7 cM, 2.6 cM, 2.5 cM, 2.4 cM, 2.3 cM, 2.2 cM, 2.1 cM, 2.0 cM, about 1.9 cM, about 1.8 cM, about 1.7 cM, about 1.6 cM, about 1.5 cM, about 1.4 cM, about 1.3 cM, about 1.2 cM, about 1.1 cM, about 1.0 cM, about 0.9 cM, about 0.8 cM, about 0.7 cM, about 0.6 cM, about 0.5 cM, about 0.4 cM, about 0.3 cM, about 0.2 cM, about 0.1 cM, or less than 0.1 cM.

As used herein, the term "mass selection" refers to a form of selection in which individual plants are selected and the next generation propagated from the aggregate of their seeds.

As used herein, the terms "mutant" or "mutation" refer to a gene, cell, or organism with an abnormal genetic constitution that may result in a variant phenotype.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "self-crossing", "self-pollinated" or "self-pollination" means the pollen of one flower on one plant is applied (artificially or naturally) to the ovule (stigma) of the same or a different flower on the same plant.

As used herein, the term "variety" refers to a subdivision of a species, consisting of a group of individuals within the species that are distinct in form or function from other similar arrays of individuals.

As used herein, the term "QTL" is used herein in its art-recognized meaning. A QTL may for instance comprise one or more genes of which the products confer the genetic resistance or tolerance. Alternatively, a QTL may for instance comprise regulatory genes or sequences of which the products influence the expression of genes on other loci in the genome of the plant thereby conferring the virus resistance or tolerance. The QTLs of the present invention may be defined by indicating their genetic location in the genome of the respective virus-resistant accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

As used herein, the terms "molecular marker" refer to an indicator that is used in methods for visualizing differences in characteristics of nucleic acid sequences. Examples of such indicators are restriction fragment length polymorphism (RFLP) markers, amplification fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed quite easily by the person skilled in the art using common molecular techniques. It is noted in this respect that specific positions in a chromosome can indeed be defined with respect to markers, such as SNPs, insofar as the flanking sequences of said markers are defined in order to unambiguously position them on the genome. The present inventors have used SNPs markers, identified by their flanking sequences, present in the *C. pepo* genome, to discriminate between introgressed and endogenously residing sequences and to track down the introgressed sequences conferring the ToLCNDV tolerance or resistance in the *C. pepo* genome.

As used herein, a "chromosomal region" or "chromosomal interval" delimited by two markers (e.g. SNPs) X and Y refers to the section of the chromosome lying between the positions of these two markers and comprising said markers, therefore the nucleotide sequence of this chromosomal region or interval begins with the nucleotide corresponding to marker X and ends with the nucleotide corresponding to marker Y, i.e. the markers are comprised within the region or interval they delimit, in the sense of the invention.

Plant Diseases Resistance

Plant disease resistance is crucial to the reliable production of food, and it provides significant reductions in agricultural use of fuel, water, land and other inputs. There are numerous examples of devastating plant disease impacts (see Irish Potato Famine, Chestnut blight) as well as recurrent severe plant disease issues (see Rice blast, Soybean cyst nematode, Citrus canker). It is estimated that diseases typically reduce plant yields by at least 10% every year.

Plant disease resistance derives both from pre-formed defenses and from infection-induced responses mediated by the plant immune system. Disease outcome is determined by the three-way interaction of the pathogen, the plant, and the environmental conditions (an interaction known as the disease triangle). Defense-activating compounds can move cell-to-cell and systemically through the plant vascular system, but plants do not have circulating immune cells so most cell types in plants retain the capacity to express a broad suite of antimicrobial defenses. Although obvious qualitative differences in disease resistance can be observed when some plants are compared (allowing classification as "resistant" or "susceptible" after infection by the same pathogen strain at similar pathogen pressure in similar environments), a gradation of quantitative differences in disease resistance is more typically observed between plant lines or genotypes.

Preformed structures and compounds that contribute to resistance in plants include, but are not limited to, plant cuticle/surface, plant cell walls, antimicrobial chemicals (e.g., glucosides, saponins), antimicrobial proteins, enzyme inhibitors, detoxifying enzymes that break down pathogen-derived toxins, receptors that perceive pathogen presence and active inducible plant defenses. Inducible plant defenses that are generated upon or after infection include, but are not limited to, cell wall reinforcement (e.g., increased callose, lignin, suberin, cell wall proteins), antimicrobial chemicals (e.g., reactive oxygen species such as hydrogen peroxide, peroxynitrite, or complex phytoalexins such as genistein or camalexin), antimicrobial proteins (e.g., defensins, thionins, or pathogenesis-related (PR) proteins), antimicrobial enzymes (e.g., chitinases, beta-glucanases, peroxidases), hypersensitive response (e.g., rapid host cell death response associated with defense mediated by resistance genes), and post-translation gene silencing.

Plant immune systems show some mechanistic similarities and apparent common origin with the immune systems of insects and mammals, but also exhibit many plant-specific characteristics. As in most cellular responses to the environment, defenses are activated when receptor proteins directly or indirectly detect pathogen presence and trigger ion channel gating, oxidative burst, cellular redox changes, protein kinase cascades, and/or other responses that either directly activate cellular changes (such as cell wall reinforcement), or activate changes in gene expression that then elevate plant defense responses.

Plants, like animals, have a basal immune system that includes a small number of pattern recognition receptors that are specific for broadly conserved microbe-associated molecular patterns (MAMPs, also called pathogen-associated molecular patterns or PAMPs). Examples of these microbial compounds that elicit plant basal defense include bacterial flagellin or lipopolysaccharides, or fungal chitin. The defenses induced by MAMP perception are sufficient to repel most potentially pathogenic microorganisms. However, pathogens express effector proteins that are adapted to allow them to infect certain plant species; these effectors often enhance pathogen virulence by suppressing basal host defenses.

Importantly, plants have evolved R genes (resistance genes) whose products allow recognition of specific pathogen effectors, either through direct binding of the effector or by recognition of the alteration that the effector has caused to a host protein. R gene products control a broad set of disease resistance responses whose induction is often sufficiently rapid and strong to stop adapted pathogens from further growth or spread. Plant genomes each contain a few hundred apparent R genes, and the R genes studied to date usually confer specificity for particular strains of a pathogen species. As first noted by Harold Flor in the mid-20th century in his formulation of the gene-for-gene relationship, the plant R gene and the pathogen "avirulence gene" (effector gene) must have matched specificity for that R gene to confer resistance. The presence of an R gene can place significant selective pressure on the pathogen to alter or delete the corresponding avirulence/effector gene. Some R genes show evidence of high stability over millions of years while other R genes, especially those that occur in small clusters of similar genes, can evolve new pathogen specificities over much shorter time periods.

The use of receptors carrying leucine-rich repeat (LRR) pathogen recognition specificity domains is common to plant, insect, jawless vertebrate and mammal immune systems, as is the presence of Toll/Interleukin receptor (TIR) domains in many of these receptors, and the expression of defensins, thionins, oxidative burst and other defense responses (Jones and Dangl, 2006, Nature, 444:323-329; Ting et al., 2008, Nat Rev Immunol., 8:372-379, which are incorporated herein by reference in their entireties).

Some of the key endogenous chemical mediators of plant defense signal transduction include salicylic acid, jasmonic acid or jasmonate, ethylene, reactive oxygen species, and nitric oxide. Numerous genes and/or proteins have been identified that mediate plant defense signal transduction (Hammond-Kosack and Parker, 2003, Curr Opin Biotechnol., 14:177-193). Cytoskeleton and vesicle trafficking dynamics help to target plant defense responses asymmetrically within plant cells, toward the point of pathogen attack.

Plant immune systems can also respond to an initial infection in one part of the plant by physiologically elevating the capacity for a successful defense response in other parts of the plant. These responses include systemic acquired resistance, largely mediated by salicylic acid-dependent pathways, and induced systemic resistance, largely mediated by jasmonic acid-dependent pathways. Against viruses, plants often induce pathogen-specific gene silencing mechanisms mediated by RNA interference. These are primitive forms of adaptive immunity.

In a small number of cases, plant genes have been identified that are broadly effective against an entire pathogen species (against a microbial species that is pathogenic on other genotypes of that host species). Examples include barley MLO against powdery mildew, wheat Lr34 against leaf rust, and wheat Yr36 against stripe rust. An array of mechanisms for this type of resistance may exist depending on the particular gene and plant-pathogen combination.

Other reasons for effective plant immunity can include a relatively complete lack of co-adaptation (the pathogen and/or plant lack multiple mechanisms needed for colonization and growth within that host species), or a particularly effective suite of pre-formed defenses.

Disease resistant plants offer an effective, safe, and relatively less expensive method of controlling many crop diseases. Most available commercial varieties of crop plants bear resistance to at least one, and often several, pathogens. Resistant or immune varieties are critically important for low-value crops in which other controls are unavailable, or their expense makes them impractical. Much has been accomplished in developing disease-resistant varieties of field crops, vegetables, fruits, turf grasses, and ornamentals.

Resistance to disease varies among plants. It may be either total (a plant is immune to a specific pathogen) or partial (a plant is tolerant to a pathogen, suffering minimal injury). The two broad categories of resistance to plant diseases are vertical (specific) and horizontal (nonspecific). A plant variety that exhibits a high degree of resistance to a single race, or strain, of a pathogen is said to be vertically resistant; this ability usually is controlled by one or a few plant genes. Horizontal resistance, on the other hand, protects plant varieties against several strains of a pathogen, although the protection is not as complete. Horizontal resistance is more common and involves many genes.

Several means of obtaining disease-resistant plants are commonly employed alone or in combination. These include, but are not limited to, introduction from an outside source, selection, and induced variation. All three may be used at different stages in a continuous process; for example, varieties free from injurious insects or plant diseases may be introduced for comparison with local varieties. The more promising lines or strains are then selected for further propagation, and they are further improved by promoting as much variation as possible through hybridization or special treatment. Finally, selection of the plants showing greatest promise takes place.

Methods used in breeding plants for disease resistance are similar to those used in breeding for other characters. It is necessary to know as much as possible about the nature of inheritance of the resistant characters in the host plant and the existence of physiological races or strains of the pathogen.

The techniques of genetic engineering can be used to manipulate the genetic material of a cell in order to produce a new characteristic in an organism. Genes from plants, microbes, and animals can be recombined (recombinant DNA) and introduced into the living cells of any of these organisms. The production of pathogen-resistant transgenic plants has been achieved by this method. Certain genes are inserted into the plant's genome that confer resistance to such pathogens as viruses, fungi, and insects.

Begomoviruses

The taxonomic family Geminiviridae includes some of the most important plant viruses causing severe diseases in agricultural, ornamental and horticultural crops. Geminiviruses generally are characterized by the unique twin shape of a fused icosahedral viral particle. Geminiviruses are plant viruses which have ambisense single-stranded circular DNA genomes. The genome can either be a single component of 2500-3000 nucleotides, or two similar-sized components. They generally have an elongated, geminate capsid with two incomplete T=1 icosahedra joined at the missing vertex. The capsids range from 18-20 nm in diameter with a length of about 30 nm. Viruses with bipartite genomes (begomoviruses only) have these components separated into two different particles, therefore more than one virus particle is required to infect a cell. Transmission of these viruses can be via leafhoppers (mastreviruses, curtoviruses) or via species of whitefly (begomoviruses) or via treehoppers (topocuviruses).

The geminiviruses are responsible for a significant amount of crop damage worldwide. Diseases caused by these viruses have long been recognized as a limitation to the cultivation of several important crops, including maize, cassava, bean, squash, cucurbits, and tomato. Epidemics of geminivirus diseases have arisen due to a number of factors, including the recombination of different geminiviruses co-infecting a plant, which enables novel, possibly virulent viruses to be developed. Other contributing factors include the transport of infected plant material to new locations, expansion of agriculture into new growing areas, and the expansion and migration of vectors that can spread the virus from one plant to another.

Geminiviruses comprise a large and diverse family of viruses that infect a wide range of important monocotyledonous and dicotyledonous crop species and cause significant yield losses. Geminiviruses are classified into four genera: genus Mastrevirus (e.g., Maize streak virus), genus Curtovirus (e.g., Beet curly top virus), genus Begomovirus (e.g., SLCV), and genus Topocuvirus (Tomato pseudo-curly top virus).

The genus Begomovirus contains more than 200 viral species (Fauquet et al, 2008, Archives of Virology, 153(4): 783-821) and belong to the taxonomic family Geminiviridae. They are plant viruses that as a group have a very wide host range. Natural hosts of begomoviruses are plant species in which the virus can replicate, cause systemic infection, and encapsidate, and from which virions are ingested and transmitted to a susceptible host by the whitefly vector (Funayama, 2001). Worldwide they are responsible for a large amount of economic damage to many important agronomic and horticultural crops such as tomatoes, beans, squash, cucurbits, cassava and cotton in subtropical and tropical regions of Americas, Africa and Asia. Begomoviruses cause stunting of plants, curling and yellowing of the leaves and low yield of fruits (Saeed et al. 2007, Journal of General Virology, 88:2881-2889). Morphologically, begomovirus particles are non-enveloped. The nucleocapsid is 38 nm long and 15-22 nm in diameter. While particles have basic isocahedral symmetry, they consist of two incomplete icosahedra—missing one vertex—joined together. There are 22 capsomeres per nucleocapsid. Begomovirus species has single stranded closed circular DNA. Most begomoviruses have a bipartite genome, meaning that the genome is segmented into two segments (referred to as DNA A and DNA B) that are packaged into separate particles. Both segments are generally required for successful symptomatic infection in a host cell, but DNA B is dependent for its replication upon DNA A, which can in some begomoviruses apparently cause infections on its own.

Tomato leaf curl New Delhi virus (ToLCNDV), a begomovirus, can cause severe losses in many crops. It was first described on tomatoes in India in 1995, but subsequently, many reports of damages to cucurbit crops have also been made, first in other Asian countries and more recently in Europe: in September 2012, symptoms have been observed on squash in Spain, first in Murcia region, then, by May 2013 in Almeria province, not anymore in squash but also on melon and pumpkins. ToLCNDV is transmitted by the whitefly *Bemisia tabacci*. Symptoms include curling and severe mosaic of the young leaves, very short internodes, fruit skin roughness and longitudinal cracking of the fruits, plant growth reduction and fruit yield reduction, leading to catastrophic losses.

Cucurbita

Cucurbita is a plant genus of the Cucurbitaceae family. Most of the plants in this genus are annual vines. Many species have large, yellow or white flowers. The stems are hairy and pentangular. Tendrils are present at 90° to the leaf petioles at nodes. Leaves are exstipulate alternate simple palmately lobed or palmately compound. The flowers are unisexual, with male and female flowers on different plants (dioecious) or on the same plant (monoecious). The female flowers have inferior ovaries. The fruit is often a kind of berry called a pepo.

Curcurbita genus plants include the following 13 species groups: *C. argyrosperma* or *C. mixta* group (e.g. *C. kellyana, C. palmeri, C. sororia* species), *C. digitata* group (e.g. *C. californica, C. cordata, C. cylindrata* and *C. palmata* species), *C. ecuadorensis* group, *C. ficifolia* group, *C. foetidissima* group (e.g. *C. scabridifolia* species), *C. galeottii* group, *C. lundelliana* group, *C. maxima* group (e.g. *C. andreana* species), *C. moschata* group, *C. okeechobeensis* group (e.g. *C. martinezii* species), *C. pedatifolia* group (e.g. *C. moorei* species), *C. pepo* group (e.g. *C. fraterna* and *C. texana* species), and *C. radicans* group (e.g. including *C. gracillor* species).

Squash

Squash is the common name for a collection of plants that produce edible seeds, fruits and flowers. Squashes generally refer to four species of the genus *Cucurbita* native to Mexico and Central America, also called marrows depending on variety or the nationality of the speaker. It is also natively grown in other parts of North America, and in Europe, India, and Australia. In North America, squash is loosely grouped into summer squash or winter squash, as well as autumn squash (another name is cheese squash) depending on whether they are harvested as immature vegetables (summer squash) or mature vegetables (autumn squash or winter squash). Gourds are from the same family as squashes. Well known types of squash include the pumpkin and zucchini. Giant squash are derived from *Curcurbita maxima* and are routinely grown to weights nearing those of giant pumpkins. Non-limiting examples of squash species include, *C. maxima* (winter squash), *C. mixta* (cushaw squash), *C. moschata* (winter crookneck squash, e.g., butternut squash), *C. pepo* var. *pepo* (most pumpkins, acorn squash), *C. pepo* var. *melopepo* (e.g., summer squash (bush summer squash zucchini)), ambercup squash, autumn cup squash, banana squash, buttercup squash, carnival squash, delicata squash, gold nugget squash, kabocha squash, spaghetti squash, sweet dumpling squash, hubbard squash, and turban squash.

Winter squashes are the mature fruits of three Cucurbit species: *Cucurbita maxima, Cucurbita moschata* and *Cucurbita pepo*. Fruit from winter squash varieties are grown to physiological maturity and typically stored for consumption during the winter months or used for ornamental purposes. Examples of common winter squashes are acorn, butternut, hubbard, and spaghetti squash, as well as the Halloween type pumpkins. *Cucurbita maxima* is one of the most diverse domesticated species, perhaps with more cultivated forms than any other crop. This species originated in South America from the wild *C. maxima* ssp. *andreana* over 4000 years ago. Different squash types of this species were introduced into North America as early as the 16th century. By the early 19th century, at least three varieties are known to have been commercially introduced in North America from seeds obtained from Native Americans. Secondary centers of diversity include India, Bangladesh, Burma, and possibly the southern Appalachians. Non-limiting examples of *Cucurbita maxima* include, Banana squash, Buttercup squash, Jarrandale pumpkin, Kabocha, Lakota squash, Ankara squash, and Hubbard squash. Candyroaster landrace *Cucurbita moschata* is a species that includes some varieties of squash and pumpkin. *C. moschata* squash are generally more tolerant of hot, humid weather than *C. maxima* or *C. pepo*. They also generally display a greater resistance to disease and insects, especially to the squash vine borer. Non-limiting examples of *C. moschata* include, butternut squash, Dickinson field pumpkin, Kentucky field pumpkin, Long Island cheese pumpkin, Calabaza pumpkin, Seminole pumpkin, Neck pumpkin, and Long of Naples squash. *Cucurbita pepo* is the main economic squash species. It includes varieties of squash, gourd, and pumpkin. Non-limiting example of *Cucurbita pepo* include, Acorn squash, Delicata squash, Gem squash, Heart of gold squash, Pattypan squash, Some types of Pumpkin, Spaghetti squash, Sweet dumpling squash, Yellow crookneck squash, Yellow summer squash, and Zucchini.

Most summer squash varieties are *Cucurbita pepo*, and their fruits are typically harvested and consumed at an immature stage. The flowers of summer squash can also be harvested for consumption. There are many types of summer squash, including yellow crookneck, yellow straightneck, scallop, Lebanese, and green and gray zucchini. Green zucchini is the type of *C. pepo* squash preferred by consumers in Europe and many parts of the North America, as well as in other regions. Unlike winter squashes, summer squash fruit have a short shelf life, and are typically consumed within days of harvest. Because of the extended ability to ship produce over long distances there are some markets where the terms "summer" and "winter" squash no longer reflect a restriction on availability and all types can be found in these markets year round.

Isolated Virus Strain, Viral Nucleic Acid Sequences and Amino Acid Sequences

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information (http://www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (B) of 10, a cutoff of 100, M=5, N=−4, and a comparison of both strands. For amino acid sequences, the BLASTP program uses as defaults a word length (W) of 3, an expectation (B) of 10, and the BLOSUM62 scoring matrix (see Henikoff & Henikoff, 1989, Proc. Natl. Acad. Sci, USA 89:10915).

In some embodiments, the ToLCNDV virus comprises or consists of the sequence SEQ ID NO: 1 (NCBI Reference Number KF749223.1, update May 22, 2014) or SEQ ID NO: 2 (NCBI Reference Number KF749225.1, update May 22, 2014). In some embodiments, the ToLCNDV virus comprises or consists of a sequence at least 80, 85, 90, 95, 96, 97, 98, 99% identical to the sequence SEQ ID NO: 1 or SEQ ID NO: 2.

Phylogenetic analysis based on the nucleotide sequence or the amino acid sequence can be performed to determine the relationships between the isolated virus and other begomoviruses.

It is understood that homologies may be large when two sequences are compared over a small comparison window since local regions of sequence similarity can often be found when two long nucleotide sequences are compared. However, the skilled person is aware that sequence homology requires the establishment of common motifs between the sequences, among which the sequence identity may locally be as high as 35 to 100%, but may be as low as 10-20% in other parts of the sequence. Thus, when reference is made herein that a sequence has a nucleotide sequence and/or an amino acid sequence homology of at least 80% to any one of SEQ ID NO: 1 or 2, this may refer to the sequence homology between regions amongst common motifs, where homology is greatest, but also between the other part the sequence. Note that sequence homologies may differ between the various genes or proteins in the genome.

A ToLCNDV can be identified by the percentages of homology of the viral proteins or nucleic acids to be identified in comparison with viral proteins or nucleic acids identified herein. It is generally known that virus species often constitute a quasi species wherein a cluster of said viruses displays heterogeneity among its members. Thus it is expected that each isolate may have a somewhat different percentage homology with the sequences of the isolate as provided herein. Therefore, other viral isolates that exhibit sufficient sequence homology to viral proteins or nucleic acids identified herein are considered to belong to the same virus. Similar to other viruses, a certain degree of variation can be expected to be found between ToLCNDV viruses isolated from different sources. Suitable nucleic acid genome fragments each useful for phylogenetic analyses are for example any portion of nucleic acid sequences of the virus, such as the fragment of the Large, Medium and Small RNA fragments, or fragment of any genes (e.g., nonstructural protein NSs gene, nucleocapsid protein N gene, glycoprotein G gene, RNA dependent polymerase (RdRp) gene). For example, a suitable nucleic acid genome fragment for identifying a ToLCNDV comprises or consists of sequence SEQ ID NO: 3, (i.e. a sequence comprising a part of the coat protein (CP) and the AC2 and AC3 genes).

The term "variant" with respect to a protein refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. General texts which describe molecular biological techniques, which are applicable to the present invention, such as cloning, mutation, and the like, include Berger and Kimmel, Guide to Molecular Cloning Techniques, Methods in Enzymology, Vol. 152 Academic Press, Inc., San Diego, Calif. ("Berger"); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating the present genes etc. Thus, the invention also encompasses using known methods of protein engineering and recombinant DNA technology to improve or alter the characteristics of the proteins expressed in algae. Various types of mutagenesis can be used to produce and/or isolate variant nucleic acids that encode for protein molecules and/or to further modify/mutate the proteins of the present invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Methods of cloning said genes are known in the art. The gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Proteins of an isolated ToLCNDV may be separated by electrophoresis using for instance Tricine-SDS-PAGE (Schagger and Von Jagow, 1987) or Glycine-SDS-PAGE (Laemmli, 1970).

Other electrophoresis systems that are capable of resolving the various proteins comprised in the virus isolate, or transcribed from its genome and expressed in a suitable expression system, may of course also be employed, such as non-denaturing gel electrophoresis. The area of the PAGE gel including the target protein may be excised and the target polypeptides may be eluted therefrom, for instance by using an Elutrap® device (Schleicher & Schuell, Dassel, Germany).

A target protein may be identified by its mobility relative to reference polypeptides in a gel. To increase purity the eluted protein may be run on a second SDS-PAGE gel and eluted a second time. The protein or peptide contained in the excised gel fragment may then be eluted again and is suitable for use in immunization or in protein sequencing.

Proteins of an isolated ToLCNDV may also be purified by affinity chromatography using an antibody (such as a monoclonal antibody) that specifically binds to a protein of the present isolated virus. The antibody may be covalently coupled to solid supports such as celluloses, polystyrene, polyacrylamide, cross-linked dextran, beaded agarose or controlled pore glass using bifunctional coupling agents that react with functional groups on the support and functional groups (i.e., reactive amino acid side chains) on the antibody molecule. Such methods are readily available to the skilled person. The resulting antibody-bearing solid phase is contacted with purified or partially purified virus under reducing conditions using pH, ionic strength, temperature and residence times that permit the protein of interest to bind to the immobilized antibody. The virus or protein is eluted from the column by passing an eluent that dissociates hydrogen bonds through the bed. Buffers at specific pH or NaCl solutions above about 2 M are commonly used eluents.

Methods for carrying out affinity chromatography using antibodies as well as other methods for immunoaffinity purification of proteins (such as viral capsid proteins) are well known in the art (see e.g., Harlow and Lane, 1988).

Methods of Diagnosing Plants

Diagnostic means and methods can be employed in the detection of ToLCNDV virus in a plant of the genus *Cucurbita*. The detection of ToLCNDV is performed with reagents that are most specific for ToLCNDV virus. This by no means however excludes the possibility that less specific, but sufficiently cross-reactive reagents are used instead, for example because they are more easily available and sufficiently address the task at hand.

Methods of Detection Based on Nucleic Acid Detection

The presence or absence of one or more ToLCNDV-specific nucleic acid sequences may be detected by extracting nucleic acids from a plant or plant part and detecting the presence or absence of one or more ToLCNDV-specific nucleic acids. For example, presence or absence of one or more ToLCNDV-specific nucleic acids may be detected as disclosed in examples 2 or 3.

The ToLCNDV-specific nucleic acid sequences may be in one or more different regions. The regions may be of one or more different genes of a ToLCNDV. A suitable biological sample can be prepared by any method, wherein the sample contains a template selected from the group consisting of DNA, RNA, and otherwise, so long as the template fits the criteria for amplification purposes by those skilled in the art. For example, the method can comprise amplification of said ToLCNDV-specific nucleic acid sequence with one or more ToLCNDV-specific primer sets. The amplification method used can be PCR or RT-PCR, wherein the RT-PCR is performed using a real time PCR technique. In another method, the detecting step comprises nucleic acid hybridization between a ToLCNDV-specific nucleic acid sequence with a ToLCNDV-specific probe. The nucleic acid hybridization may be a Northern blot or a Southern blot. One skilled in the art will be able to design suitable probe for this purpose.

By recombinant DNA technology it is possible to produce probes that directly or indirectly hybridize to the viral nucleic acids, (e.g., viral RNA, complement thereof, or cDNA produced therefrom by reverse transcription), which can be used in assays for the detection of the virus. Nucleic acid amplification techniques allow the amplification of fragments of viral nucleic acids, which may be present in very low amounts.

The oligonucleotide primers for PCR may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in e.g. U.S. Pat. No. 4,458,066. The primers may be labeled, if desired, by incorporating means detectable by for instance spectroscopic, fluorescence, photochemical, biochemical, immunochemical, or chemical means.

Template-dependent extension of the oligonucleotide primer(s) is catalyzed by a polymerizing agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, T4 DNA polymerase, and Taq DNA polymerase. The reaction conditions for catalyzing DNA synthesis with these DNA polymerases are known in the art.

The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

In order to develop nucleic acid-based detection methods, virus-specific sequences must be determined for which primers or probes may then be developed. For example, to detect ToLCNDV by nucleic acid amplification and/or probe hybridization, the viral genomic RNA was isolated from purified virus, reverse transcribed into cDNA and directly cloned and/or sequenced. Using either the cloned nucleic acid as a hybridization probe, using sequence information derived from the clone, or by designing degenerative primers based on the amino acid sequence of the ToLCNDV, nucleic acid hybridization probes and/or nucleic acid amplification primers may be designed an used in a detection assay for detecting the presence of the virus in a sample as defined herein.

Methods in which nucleic acids are detected can in principle be performed by using any nucleic acid amplification method, such as the Polymerase Chain Reaction (PCR; Mullis and Faloona, 1987; U.S. Pat. Nos. 4,683,195; 4,683,202; and 4,800,159) or by using amplification reactions such as Ligase Chain Reaction (LCR; Barany, 1991; EP 0 320 308), Self-Sustained Sequence Replication (35R; Guatelli et al., 1990), Strand Displacement Amplification (SDA; Walker et al., 1992; U.S. Pat. Nos. 5,270,184 and 5,455,166), Transcriptional Amplification System (TAS; Kwoh et al., 1989), Q-Beta Replicase (Lizardi et al., 1988), Rolling Circle Amplification (RCA; U.S. Pat. No. 5,871,921), Nucleic Acid Sequence Based Amplification (NASBA; Compton, 1991), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of nucleic acids.

ToLCNDV is a bipartite DNA virus, a suitable detection method may comprise isolating the viral nucleic acids from a sample, for instance from an infected plant, a plant suspected to be infected, by using methods known per se to the skilled person (e.g. Yazdani-Khamened et al., 2013, New Disease Reports, 28, 17; Heydarnejad et al., 2009, Arch Virol, 154:1015-1018; Anfoka et al., 2009, Plant Pathology, 58, 754-762) or commercially available systems (e.g. the SLCV immunostrip from AGDIA Inc., the TAS-ELISA for SLCV detection from DSMZ GmbH, Germany, or the DAS-ELISA for TYLCV detection from BIOREBA AG, Switzerland).

Total DNA may for instance be extracted from a plant, or any part of a plant, e.g., leaf material or protoplasts of plant cells and the total DNA, or specifically the viral genomic DNA, or a part thereof. The DNA obtained may be PCR amplified by using for instance Pfu and Taq DNA polymerases and amplification primers specific for the viral genomic DNA sequences.

In order to amplify a nucleic acid sequence with a small number of mismatches to one or more of the amplification primers, an amplification reaction may be performed under conditions of reduced stringency (e.g. a PCR amplification using an annealing temperature of 38° C., or the presence of 3.5 mM MgCl2). The person skilled in the art will be able to select conditions of suitable stringency.

The primers herein are selected to be "substantially" complementary (i.e. at least 65%, at least 70%, at least 80%, at least 90%, at least 95% perfectly complementary) to their target regions present on the different strands of each specific sequence to be amplified. It is possible to use primer sequences containing e.g. inositol residues or ambiguous bases or even primers that contain one or more mismatches when compared to the target sequence. In general, sequences that exhibit at least 65%, at least 70%, at least 80%, at least 90%, at least 95%, at least 99% homology with the target DNA or RNA oligonucleotide sequences, are considered suitable for use in a method of the present invention. Sequence mismatches are also not critical when using low stringency hybridization conditions. The detection of the amplification products can in principle be accomplished by any suitable method known in the art. The amplified fragments may be directly stained or labeled with radioactive labels, antibodies, luminescent dyes, fluorescent dyes, or enzyme reagents. Direct DNA stains include for example intercalating dyes such as alcidine orange, ethidium bromide, ethidium monazite or Hoechst dyes. Alternatively, the DNA or RNA fragments may be detected by incorporation of labeled dNTP bases into the synthesized fragments. Detection labels which may be associated with nucleotide bases include e.g. fluorescein, cyanine dye, digoxigenin (DIG) or bromodeoxyuridine (BrdUrd).

When using a probe-based detection system, a suitable procedure for use in the present invention may for example comprise an enzyme immunoassay (EIA) format (Jacobs et al., 1997). For performing a detection by manner of the EIA procedure, either the forward or the reverse primer used in the amplification reaction may comprise a capturing group, such as a biotin group for immobilization of target DNA PCR amplicons on e.g. a streptavidin coated microtiter plate wells or streptavidin coated Dynabeads® (Dynal Biotech, Oslo, Norway) for subsequent EIA detection of target DNA-amplicons. The skilled person will understand that other groups for immobilization of target DNA PCR amplicons in an EIA format may be employed.

Probes useful for the detection of the target nucleic acid sequences as disclosed herein preferably bind only to at least a part of the nucleic acid sequence region as amplified by the nucleic acid amplification procedure. Also the complementary nucleotide sequences, whether DNA or RNA or chemically synthesized analogues, of the target nucleic acid may suitably be used as type-specific probes in a method of the invention, provided that such a complementary strand is amplified in the amplification reaction employed.

Suitable detection procedures for use herein may for example comprise immobilization of the amplicons and probing the nucleic acid sequences thereof by e.g. Northern and Southern blotting. Other formats may comprise an EIA format as described above. To facilitate the of binding, the specific amplicon probes may comprise a label moiety such as a fluorophore, a chromophore, an enzyme or a radio-label, so as to facilitate monitoring of binding of the probes to the reaction product of the amplification reaction. Such labels are well known to those skilled in the art and include, for example, fluorescein isothiocyanate (FITC), β-galactosidase, horseradish peroxidase, streptavidin, biotin, digoxigenin, $^{35}S$, $^{14}C$, $^{32}P$ or $^{125}I$. Other examples will be apparent to those skilled in the art.

Detection may also be performed by a so called reverse line blot (RLB) assay, such as for instance described by Van den Brule et al. (2002). For this purpose RLB probes can be synthesized with a 5' amino group for subsequent immobilization on e.g. carboxyl-coated nylon membranes. The advantage of an RLB format is the ease of the system and its speed, thus allowing for high throughput sample processing.

The use of nucleic acid probes for the detection of RNA or DNA fragments is well known in the art. Mostly these procedures comprise the hybridization of the target nucleic acid with the probe followed by post-hybridization washings. Specificity is typically the function of post-hybridization washes, the critical factors being the ionic strength and temperature of the final wash solution. For nucleic acid hybrids, the Tm can be approximated from the equation of Meinkoth and Wahl (1984): Tm=81.5° C.+16.6 (log M)+0.41 (% GC)−0.61 (% form)−500/L; where M is the molarity of monovalent cations, % GC is the percentage of guanosine and cytosine nucleotides in the nucleic acid, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, the hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, 1993; Ausubel et al., 1998.

Oligonucleotide probes for the detection of ToLCNDV-specific nucleic acids can be produced. The probes are selected to be "substantially" complementary to a single stranded RNA molecule, or to one of the strands of the double stranded nucleic acids generated by an amplification reaction of the invention. Preferably the probes are substantially complementary to the optionally immobilized (e.g. biotin labeled) antisense strands of the amplicons generated from the target RNA or DNA.

It is allowable for detection probes of the present invention to contain one or more mismatches to their target sequence. In general, sequences that exhibit at least 65%, at least 70%, at least 75%, at least 80% homology with the target oligonucleotide sequences are considered suitable for use in a method of the present invention.

The detecting step can comprise amplification of one or more ToLCNDV-specific nucleic acid sequences, using one or more ToLCNDV-specific primer sets, and determining the presence or absence of said ToLCNDV-specific nucleic acid sequences. In one embodiment, the ToLCNDV-specific nucleic acid sequences can be of one or more different genes in the biological sample. The biological sample can be prepared by any method, wherein the sample contains a template selected from the group consisting of DNA, RNA, and otherwise, so long as the template fits the criteria for amplification purposes by those skilled in the art. The template can be RNA, and amplified through RT-PCR. The RT-PCR can be real time RT-PCR.

Alternatively, in the detection method based on nucleic acid detection, and the detecting step comprises detecting a ToLCNDV-specific nucleic acid sequence by nucleic acid hybridization. The ToLCNDV-specific nucleic acid sequence can be from purified RNA from ToLCNDV. The ToLCNDV-specific nucleic acid sequence can be from DNA. The probe for hybridization can be derived from any other nucleic acid sequence of ToLCNDV.

Method of Screening ToLCNDV Tolerant/Resistant or Susceptible Plants of the Genus *Cucurbita*

The present invention provides a method of screening for a plant population, plant, plant tissue or plant cell of the genus *Cucurbita* that is resistant, tolerant, or susceptible to ToLCNDV, comprising:

a) growing said plant population, plant, plant part, plant tissue or plant cell of the genus *Cucurbita,*
b) challenging said plant population, plant, plant part, plant tissue or plant cell of the genus *Cucurbita* with an infective amount of an isolated virus strain, and
c) evaluating the tolerance or resistance in the plant, plant, plant part, plant tissue and plant cell of the genus *Cucurbita.*

In some embodiment, said plant of the genus *Cucurbita* is a *Cucurbita pepo* (*C. pepo*), *Cucurbita moschata* (*C. moschata*), *Cucurbita okeechobeensis* (*C. okeechobeensis*), *Cucurbita pedatifolia* (*C. pedatifolia*) or a *Cucurbita maxima* (*C. maxima*) plant. In some embodiments, the *C. moschata* plant is 'Nigerian', 'Menina Portugal', 'Menina Brasileira', or hybrid thereof.

An infective dosage may vary between plants and between ToLCNDV-isolates tested. Theoretically, an amount of about 1 to 10, about 10 to 100, about 100 to 1000, about 1000-10000, or about 10000-100000 viral particles of said virus will be sufficient. Infection in this way may be achieved by mechanical inoculation of purified virus particles or virus nucleic acid on healthy plants. Alternatively, infection may be achieved by, for instance:

a) growing a healthy scion on a ToLCNDV-infected rootstock, or vice versa,
b) exposing a healthy plant to transmission vectors containing the virus (including infected plants, e.g. parasitic plants like cucurbit plants and *N. benthamiana*),
c) introducing into a healthy plant an expression vector harboring a coding region of the ToLCNDV virus genome, and
d) use of agro-infectious clones, such as *Agrobacterium tumefaciens* strains containing an expression vector harboring a coding region of the ToLCNDV virus genome.

Thus, in the context of the present invention, methods for challenging a plant population, plant, plant part, plant tissue or plant cell to an infective dosage of ToLCNDV are not limited to any particular method. For example, methods for challenging a plant population, plant, plant part, plant tissue or plant cell to an infective dosage of ToLCNDV can be performed as disclosed in examples 4 and 5. For example, infection may comprise mechanical inoculation of the virus on healthy plants. In one embodiment, a portion of a diseased leaf may be rubbed directly onto a leaf of a plant that is to be challenged. In an alternative procedure, an inoculum may for instance be prepared by grinding virus-containing plant tissue, e.g., young leaves showing symptoms, with a mortar and pestle, or any other suitable type of homogenizer, in for instance a buffer suitable for inoculation (e.g. a 0.03 M phosphate buffer, pH 7.7). After grinding, the obtained homogenate (the sap) can be filtered, e.g. through cheese cloth. The sap may then be inoculation, for instance by gently contacting leaves with an amount of the sap. The leaves can be pre-treated in order to damage the lower epidermis and enhance entry of the virus. This may for instance be achieved by pre-dusting the leaves with carborundum powder. Excessive wounding can be avoided. For example, a carborundum powder is used having microscopically small angular particles of silicon carbide (400-500 mesh). Carborundum powder may also be added directly to the sap, in which case the pre-treatment is omitted. The sap may, for instance, be applied by the forefinger, a pad of sap-soaked foam or fabric (e.g., a sponge pad with scouring side), or even with the pestle used for grinding, a glass spatula, a stiff brush, or a spray gun. Another method of preparing inoculum containing ToLCNDV is, soaking virus-containing plant tissue in suitable solution for a period of time wherein sufficient amount of virus is released from said plant tissue.

A plant, plant part, plant tissue or plant cell of the genus *Cucurbita* resistant or tolerant to ToLCNDV may have at least one characteristics as described below:

1) disease-symptoms in said plant, plant part, plant tissue or plant cell of the genus *Cucurbita* remain absent, delayed, reduced in severity, or more localized compared to a susceptible control plant, plant part, plant tissue or plant cell of the genus *Cucurbita,*

2) ToLCNDV nucleic acid sequences are not present, or at least quantitatively reduced in density in said plant, plant part, plant tissue or plant cell of the genus *Cucurbita* compared to a susceptible control plant, plant part, plant tissue or plant cell of the genus *Cucurbita*, and/or 3) ToLCNDV amino acids sequences are not present, or at least quantitatively reduced in density in said plant, plant part, plant tissue or plant cell of the genus *Cucurbita* compared to a susceptible control plant, plant part, plant tissue or plant cell of the genus *Cucurbita*.

To determine the severity of infection in a plant of the genus *Cucurbita*, quantitative and/or qualitative methods can be taken. In a non-limiting exemplary quantitative method, the period required for the development of certain level of disease symptoms is compared. In a non-limiting exemplary qualitative method, after a certain period, the plant is inspected for symptoms development.

In other embodiments, the presence/absence of the virus is detected in the plant, plant part, plant tissue or plant cell of the genus *Cucurbita*, and used to measure the tolerance or resistance level. Any method of virus detection in the art may in principle be used, such as the methods described above in the present invention (e.g. as described in examples 2 or 3). For instance, a method may be employed wherein an immunological detection of ToLCNDV-specific proteins by antibodies, and/or a nucleic detection of ToLCNDV-specific nucleic acid sequences by probe hybridization and/or amplification. In one embodiment, the plant of the genus *Cucurbita* is resistant or tolerant to ToLCNDV when one or more methods fail to detect the nucleic acids and/or amino acids of ToLCNDV, or when the nucleic acids and/or amino acids of ToLCNDV is detectable, but compared to that of a susceptible control plant of the genus *Cucurbita*, the nucleic acids and/or amino acids density in the tested plant of the genus *Cucurbita* is statistically higher compared to the control plant of the genus *Cucurbita*. The skilled person will understand that for such methods it is important to decontaminate the surface of the tested plant, in order to distinguish between a transmission vector, a tolerant test-plant and a resistant test plant.

In terms of severity of infection, the following results may be obtained. If, after successful inoculation (e.g. after the establishment of a plant-virus contact under conditions that would result in infection in a susceptible and sensitive control plant):

i) disease-symptoms remain absent, or viral particles, or viral DNA cannot be detected, it indicates that the plant is resistant, ii) disease-symptoms are delayed or reduced in severity, or systemic low titers of viral particles or viral DNA can be detected, it indicates that the plant is partially resistant, iii) disease-symptoms are severe, but remain local, limited to the inoculated leaf and do not systemically spread beyond inoculated tissue; or viral particles, or viral DNA can only be detected locally, it indicates that the plant is hypersensitive, iv) if disease-symptoms remain absent; and viral particles, or viral DNA can be detected, it indicates that the plant is tolerant, v) if the plant develops disease-symptoms and has high systemic virus titers, then the plant is susceptible and sensitive.

Examples of such plants are the plants from which the virus of the present invention was isolated. These plants may serve as suitable control plants in methods of the present invention.

For the purpose of producing resistant or tolerant plants of the genus *Cucurbita*, and from a viewpoint of phytosanitation, only outcomes i), ii) and iii) may be considered of interest. For the purpose of obtaining plants of the genus *Cucurbita* suitable for the production of symptomless crops and products, outcome iv) may also be of particular commercial interest.

In one embodiment, said method comprises a control plant, plant part, plant tissue or plant cell of the genus *Cucurbita*, the population of which is also challenged with the virus strain, under similar environmental conditions and pest or pathogen pressure. Resistance level of the screened plant, plant part, plant tissue or plant cell of the genus *Cucurbita* is compared to the resistance level of the control plant, plant part, plant tissue or plant cell of the genus *Cucurbita*. In one further embodiment, the control plant, plant part, plant tissue or plant cell of the genus *Cucurbita* is susceptible to the virus strain, and the screening is targeting a plant, plant tissue or plant cell of the genus *Cucurbita* that is more resistant to the virus strain compared to the control plant, plant part, plant tissue or plant cell of the genus *Cucurbita*. In another further embodiment, the control plant, plant part, plant tissue or plant cell of the genus *Cucurbita* is resistant to the virus strain, and the screening is targeting a plant, plant part, plant tissue or plant cell of the genus *Cucurbita* that is more susceptible to the virus strain compared to the control plant, plant part, plant tissue or plant cell of the genus *Cucurbita*.

In one embodiment, the evaluating step comprises visual observation to determine the severity of the virus infection, using a resistance scoring system. The resistance scoring system is well known in the art. A resistance scoring system can be used to evaluate the resistance of a plant of the genus *Cucurbita* by signing a resistance score to a plant which ranges from 1 to 3, 1 to 5, or 1 to 9, et al., depending the severity of the infection or symptoms. For example, in a resistance scoring system 1 to 9, level 9 is the most resistant level (or the least symptomatic level), level 1 is the least resistant level (or the most symptomatic level), and level 5 is the intermediate level. In such a scoring system, a plant population is resistant if it has about 50%, about 55%, about 60%, about 65%, about 70%, about 75%, about 80%, about 85%, about 90%, about 95%, or about 100% of the plants in the least symptomatic levels of 7 to 9. In one embodiment, a plant population is resistant to the virus if it has greater than 60% of the plants in the least symptomatic levels of 7 to 9. In one embodiment, a plant population is obviously resistant to the virus if it has great than 70% of the plants in the least symptomatic levels of 7 to 9. In one embodiment, a plant population is highly resistant to the virus if it has greater than 80% of the plants in the least symptomatic levels of 7 to 9. In one embodiment, a plant population is extremely resistant to the virus if it has greater than 90% of the plants in the least symptomatic levels of 7 to 9. A plant population is susceptible if it has about 50%, about 55%, about 60%, about 65%, about 70%, about 75%, about 80%, about 85%, about 90%, about 95%, or about 100% of the plants in the most symptomatic levels of 1 and 2. In one embodiment, a plant population is some susceptible to the virus if it has greater than 60% of the plants in the most symptomatic levels of 1 and 2. In one embodiment, a plant population is obviously susceptible to the virus if it has great than 70% of the plants in the most symptomatic levels of 1 and 2. In one embodiment, a plant population is highly susceptible to the virus if it has greater than 80% of the plants in the most symptomatic levels of 1 and 2. In one embodiment, a plant population is extremely susceptible to the virus if it has greater than 90% of the plants in the most symptomatic levels of 1 and 2.

In another embodiment, said evaluating step comprises one or more molecular biological tests of virus density in the plants. In one embodiment, said molecular biological tests comprise testing the density of ToLCNDV-specific nucleic acid sequence and/or ToLCNDV-specific protein. For example, the molecular biological test can involve probe hybridization and/or amplification of nucleic acid (e.g., measuring viral nucleic acid density by Northern or Southern hybridization, RT-PCR) and/or immunological detection (e.g., measuring viral protein density, such as precipitation and agglutination tests, ELISA (e.g., Lateral Flow test, or DAS-ELISA, or TAS-ELISA), Western blot, RIA, immunogold labeling, immunosorbent electron microscopy (ISEM), and/or dot blot). A plant is resistant to the virus strain if it has a virus nucleic acid and/or protein density that is about 50%, about 40%, about 30%, about 20%, about 10%, about 5%, about 2%, about 1%, about 0.1%, about 0.01%, about 0.001%, or about 0.0001% of the virus nucleic acid and/or protein density in a susceptible plant. For example, a plant population is some resistant to the virus if it has a virus DNA and/or protein density that is about 10% of the DNA and/or protein density in a susceptible plant. A plant population is obviously resistant to the virus if it has a virus DNA and/or protein density that is about 1% of the DNA and/or protein density in a susceptible plant. A plant population is highly resistant to the virus if it has a virus DNA and/or protein density that is about 0.1% of the DNA and/or protein density in a susceptible plant. A plant population is extremely resistant to the virus if it has a virus DNA and/or protein density that is about 0.01% of the DNA and/or protein density in a susceptible plant.

The procedure to perform a nucleic acid hybridization, an amplification of nucleic acid (e.g., PCR) or an immunological detection (e.g., precipitation and agglutination tests, ELISA (e.g., Lateral Flow test or DAS-ELISA or TAS-ELISA), Western blot, RIA, immunogold labeling, immunosorbent electron microscopy (ISEM), and/or dot blot tests) as described below is well-known by one skilled in the art.

In one embodiment, the evaluating step comprises PCR, wherein ToLCNDV-specific primers are used to amplify one or more ToLCNDV-specific nucleic acid sequences. In one embodiment, said ToLCNDV-specific nucleic acid sequences are from the same gene of ToLCNDV. In another embodiment, said ToLCNDV-specific nucleic acid sequences are from different genes of ToLCNDV. In one embodiment, said ToLCNDV-specific nucleic acid sequences are selected from the group consisting of SEQ ID NO 1 to 3, a portion of any one of SEQ ID NOs. 1 to 3, a nucleic acid sequence that is at least about 80% homology to any one of SEQ ID NOs. 1 to 3, and combination thereof. In one embodiment, the ToLCNDV-specific primers allowing to amplify one or more ToLCNDV-specific nucleic acid sequences are selected from the group consisting of SEQ ID NO: 6 and SEQ ID NO: 7.

The PCR steps involve first the denaturation of the dsDNA at 94° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using agarose gel electrophoresis and ethidium bromide (or other nucleic acid staining).

In some embodiments the PCR amplification is done as described in Examples 2 or 3.

The invention is also directed to a method for detecting and/or selecting *Cucurbita* plants having the QTL on LG11 associated with tolerance or resistance to ToLCNDV, either homozygously or heterozygously, on the basis of the allele detection of at least one of the marker of the present invention. When present homozygously, the QTL confers tolerance or resistance to ToLCNDV. In some embodiments, the markers are chosen amongst markers SQ-0006678 (SEQ ID NO: 8), SQ-0010844 (SEQ ID NO: 9) and SQ-0000209 (SEQ ID NO: 10). In some embodiments, the detection and/or selection is made on the basis of the allele of the SQ-0010844 (SEQ ID NO: 9) and/or marker SQ-0000209 (SEQ ID NO: 10).

In some embodiments, plants bearing the introgressed sequences are selected if at least one of the following alleles is detected among allele G of marker SQ-0006678 (SEQ ID NO: 8), allele A of marker SQ-0010844 (SEQ ID NO: 9), and allele C of marker SQ-0000209 (SEQ ID NO: 10), in a genetic material sample of the plant to be selected. In some embodiments, plants bearing the introgressed sequences are selected if all of the following alleles is detected: allele G of marker SQ-0006678 (SEQ ID NO: 8), allele A of marker SQ-0010844 (SEQ ID NO: 9), and allele C of marker SQ-0000209 (SEQ ID NO: 10), in a genetic material sample of the plant to be selected.

In some embodiments, plants bearing the introgressed sequences are selected if allele A of marker SQ-0010844 (SEQ ID NO: 9) and/or allele C of marker SQ-0000209 (SEQ ID NO: 10), is/are detected in a genetic material sample of the plant to be selected.

According to one embodiment, the allele(s) of interest which is/are detected is/are present homozygously in the selected plant, i.e. no other allele of said marker(s) is present. In such a case, it can be concluded that the plant bears the introgressed sequences and is tolerant or resistant to ToLCNDV. Non-limiting detection methods are detailed above and applicable to this aspect of the invention. In another embodiment, the allele(s) of interest which is/are detected is/are present heterozygously in the selected plant.

In some embodiments, said *Cucurbita* plants are *C. pepo* plants.

The QTL responsible for the tolerance or resistance to ToLCNDV can advantageously be introduced into *Cucurbita* plants or varieties, such as *C. pepo* plants or varieties that contain other desirable genetic traits, such as resistance to another disease, early fruit maturation, drought tolerance, fruit shape, plant habit, internode length, androecy, and the like.

The markers of the invention can thus be used as detailed above, for selection plants or seed having the desired phenotype or bearing introgression sequence conferring said phenotype when present homozygously. According to one embodiment, the selection can be made on the basis of the presence of at least one or more of the following alleles: allele G of marker SQ-0006678 (SEQ ID NO: 8), allele A of marker SQ-0010844 (SEQ ID NO: 9), and allele C of marker SQ-0000209 (SEQ ID NO: 10). According to another embodiment, the selection can be made on the basis of the presence of all of the following alleles: allele G of marker SQ-0006678 (SEQ ID NO: 8), allele A of marker SQ-0010844 (SEQ ID NO: 9) and allele C of marker SQ-0000209 (SEQ ID NO: 10). According to another embodiment, the selection can be made on the basis of the presence of allele A of marker SQ-0010844 (SEQ ID NO: 9) and/or allele C of marker SQ-0000209 (SEQ ID NO: 10). The presence of these alleles indeed confirms the presence of introgressed sequences at the chromosomal locus defined by said markers.

ToLCNDV Resistant/Susceptible Plants of the Genus *Cucurbita*

Once a ToLCNDV resistant or susceptible plant is isolated from the screening as described above, it can be used for many purposes. Thus, the present invention provides plants of the genus *Cucurbita* resistant or susceptible to ToLCNDV (e.g. plants that are mentioned in FIG. 1). In some embodiment, said plant of the genus *Cucurbita* is a *Cucurbita pepo* (*C. pepo*), *Cucurbita moschata* (*C. moschata*), *Cucurbita okeechobeensis* (*C. okeechobeensis*), *Cucurbita pedatifolia* (*C. pedatifolia*) or a *Cucurbita maxima* (*C. maxima*) germplasm. In some embodiments, the *C. moschata* resistant plant is 'Nigerian', 'Menina Portugal', 'Menina Brasileira', or hybrid thereof.

Indeed, as demonstrated in the example section, the inventors identified that the *C. moschata* resistant plant 'Menina Portugal', 'Menina Brasileira' are the plants having the most interesting resistance level and harboring the same genetic locus conferring said resistance on linkage group 11 (LG11). They have then been able to introgress, into *C. pepo* genetic background, the *C. moschata* sequences (i.e. quantitative trait loci (QTLs)) conferring resistance or tolerance to ToLCNDV, thus obtaining resistant or tolerant *C. pepo* plants.

The present invention thus provides a *C. pepo* plant tolerant or resistant to ToLCNDV, wherein said plant comprises a QTL associated with tolerance or resistance to ToLCNDV on linkage group 11 (LG11).

In some embodiments, said QTL on LG11 is genetically linked to the markers SQ-0006678 (SEQ ID NO: 8), SQ-0010844 (SEQ ID NO: 9) and/or SQ-0000209 (SEQ ID NO: 10).

In some embodiments, said QTL on LG11 conferring the tolerance or resistance to ToLCNDV is located at less than 5 cM, less than 2.5 cM, less than 1 cM, or less than 0.5 cM from markers SQ-0006678 (SEQ ID NO: 8), SQ-0010844 (SEQ ID NO: 9) and/or SQ-0000209 (SEQ ID NO: 10).

In some embodiments, said QTL on LG11 is located in a locus encompassing the markers SQ-0006678 (SEQ ID NO: 8), SQ-0010844 (SEQ ID NO: 9) and/or SQ-0000209 (SEQ ID NO: 10).

In some embodiments, said QTL on LG11 is located within a chromosomal region delimited by marker SQ-0006678 (SEQ ID NO: 8) and marker SQ-0000209 (SEQ ID NO: 10). In some embodiments, said QTL on LG11 is located within a chromosomal region delimited by marker SQ-0010844 (SEQ ID NO: 9) and marker SQ-0000209 (SEQ ID NO: 10). These markers have predictive value for the phenotype of interest, i.e. the tolerance or resistance to ToLCNDV.

In some embodiments, said QTL on LG 11 conferring tolerance or resistance to ToLCNDV according to the present invention is homozygously present in the genome of the plant.

In some embodiments, said QTL on LG 11 conferring tolerance or resistance to ToLCNDV according to the present invention is heterozygously present in the genome of the plant. Such plant can be used to produce additional ToLCNDV resistant plant by self-crossing or out-crossing.

The alleles conferring the tolerance or resistance to ToLCNDV amplified by the markers SQ-0006678 (SEQ ID NO: 8), SQ-0010844 (SEQ ID NO: 9) and/or SQ-0000209 (SEQ ID NO: 10) are as described in Table 1.

TABLE 1

SNP linked to ToLCNDV resistance, location on the public Genome v3.2 and flanking sequences. The SNP is identified in bold and in brackets. R: Resistant. S: Susceptible

| SNP name | Sequence surrounding the SNP | Genome v3.2 scaffold | SNP physical position | R Allele | S Allele | Seq ID NO |
|---|---|---|---|---|---|---|
| SQ-0006678 | GTTGTAAGTCCAGCA ATAGCACCAACGCTT ATCAA[A/G]AAAGAA ACAAATTTCAAGCCT TTGGATGTAAAAGC | CP32_scaffold000045 | 837806 | G | A | 8 |
| SQ-0010844 | AAAAGAGAAAGTTG GAGGACTGAGTTGCC AAGGGC[A/C]GGCCT GGGATCTGAAGTCAT TGTGAAAATGAAAAA | CP32_scaffold000045 | 1004822 | A | C | 9 |
| SQ-0000209 | TTAACACCACCGATT CTCAGCTCCAGTAGC AAGACCAGTAGACTG CCATGGAACTCCATC GTTCTCAGAGGAAAT | CP32_scaffold000045 | 1020668 | C | A | 10 |

TABLE 1-continued SNP linked to ToLCNDV resistance, location on the public Genome v3.2
and flanking sequences. The SNP is identified in bold and in brackets.
R: Resistant. S: Susceptible

| SNP name | Sequence surrounding the SNP | Genome v3.2 scaffold | SNP physical position | R Allele | S Allele | Seq ID NO |
|---|---|---|---|---|---|---|
| | CTTCCACCGCNACCA NTTCCTCGACCACTC TTCCACTCTATCGCTC [C/A]GCTCCTCCTCTC GAAGTCAGGCTTGAA GAATTC | | | | | 15 |

Insofar as the QTL conferring tolerance or resistance to ToLCNDV can be identified by the specific alleles described in Table 1, a plant of the invention may comprise at least one of the following alleles at homozygous state: allele G of marker SQ-0006678 (SEQ ID NO: 8), allele A of marker SQ-0010844 (SEQ ID NO: 9), or allele C of marker SQ-0000209 (SEQ ID NO: 10). In another embodiment, the plant of the invention may comprise allele G of marker SQ-0006678 (SEQ ID NO: 8), allele A of marker SQ-0010844 (SEQ ID NO: 9) and allele C of marker SQ-0000209 (SEQ ID NO: 10) at homozygous state. In another embodiment, the plant may also comprise a combination of at least two of the following alleles: allele G of marker SQ-0006678 (SEQ ID NO: 8), allele A of marker SQ-0010844 (SEQ ID NO: 9), and allele C of marker SQ-0000209 (SEQ ID NO: 10) at homozygous state, such as a combination of allele A of marker SQ-0010844 (SEQ ID NO: 9) and allele C of marker SQ-0000209 (SEQ ID NO: 10) at homozygous state. In some embodiments, a plant of the invention may comprise at least one of the alleles described herein at heterozygous state.

In some embodiments, said QTL associated to tolerance or resistance to ToLCNDV is chosen from those present in the genome of a plant of the line TLG, which seeds are deposited under the NCIMB accession number 42686.

In some embodiments, said QTL associated to tolerance or resistance to ToLCNDV is as found in the genome of a plant of the line TLG, which seeds have been deposited under the NCIMB accession number 42686. Accordingly, the C. pepo plant tolerant or resistant to ToLCNDV according to the invention comprises a QTL associated with tolerance or resistance to ToLCNDV on LG11, wherein said QTL is as found in the genome of a plant of the line TLG, which seeds are deposited under the NCIMB accession number 42686.

In some embodiments, the C. pepo plant according to the invention is line TLG, which seeds are deposited under NCIMB accession number 42686.

In some embodiments, a plant according to the invention may be a progeny or offspring of a plant grown from the deposited seeds of C. pepo line TLG, deposited at the NCIMB under the accession number 42686. Plants grown from the deposited seeds are indeed homozygously tolerant or resistant to ToLCNDV, i.e., they bear in their genome the QTL associated to tolerance or resistance to ToLCNDV on LG11 as defined here above at homozygous state. They can be used to transfer this QTL in another background by any suitable methods, such as by crossing and selfing and/or backcrossing. A progeny or a plant obtained from the deposited seed can be identified by one skilled in the art, for example by using the markers SQ-0006678 (SEQ ID NO: 8), SQ-0010844 (SEQ ID NO: 9), SQ-0000209 (SEQ ID NO: 10), and any other markers within a chromosomal region delimited by marker SQ-0006678 (SEQ ID NO: 8) and marker SQ-0000209 (SEQ ID NO: 10), or a chromosomal region delimited by marker SQ-0010844 (SEQ ID NO: 9) and marker SQ-0000209 (SEQ ID NO: 10).

The present invention also provides a plant's part derived from a plant of the genus Cucurbita resistant or tolerant to ToLCNDV. In some embodiments, said plant's part derives from a C. pepo plant according to the invention, i.e. said plant's part comprises the QTL on LG11 as defined above conferring the tolerance or resistance to ToLCNDV.

In some embodiments, a part of plant is a plant cell. The invention thus provides an isolated cell of a C. pepo plant according to the invention, i.e. a cell that comprises the QTL on LG11 as defined above conferring the tolerance or resistance to ToLCNDV.

In some embodiments, the alleles conferring the tolerance or resistance to ToLCNDV are as described in Table 1. In some embodiments, the plant part according to the invention thus may comprise at least one of the following alleles at homozygous or heterozygous state: allele G of marker SQ-0006678 (SEQ ID NO: 8), allele A of marker SQ-0010844 (SEQ ID NO: 9), or allele C of marker SQ-0000209 (SEQ ID NO: 10). In some embodiments, the plant part according to the invention may comprise allele G of marker SQ-0006678 (SEQ ID NO: 8), allele A of marker SQ-0010844 (SEQ ID NO: 9) and allele C of marker SQ-0000209 (SEQ ID NO: 10) at homozygous or heterozygous state. In some embodiments, the plant part according to the invention may also comprise a combination of at least two of the following alleles: allele G of marker SQ-0006678 (SEQ ID NO: 8), allele A of marker SQ-0010844 (SEQ ID NO: 9), and allele C of marker SQ-0000209 (SEQ ID NO: 10) at homozygous or heterozygous state, such as a combination of allele A of marker SQ-0010844 (SEQ ID NO: 9) and allele C of marker SQ-0000209 (SEQ ID NO: 10) at homozygous or heterozygous state.

In some embodiments, the QTL or allele(s) as described here above are chosen from those present in the genome of a plant corresponding to the deposited material TLG (NCIMB accession number 42686).

In some embodiments, the QTL or allele(s) as described here above are as found in the genome of a plant corresponding to the deposited material TLG (NCIMB accession number 42686).

A plant cell of the invention may have the capacity to be regenerated into a whole plant, said plant having a commercially acceptable fruit quality.

Alternatively, the invention is also directed to plant cells which are not regenerable, and thus not capable of giving rise to a whole plant.

According to another embodiment, the plant part is any other part of a plant according to the invention; it may be in particular seeds, reproductive material, roots, flowers, fruits, rootstock or scion. Such a part comprises a cell as defined above.

The present invention also provides seed derived from a plant population, plant, plant part, plant tissue or plant cell of the genus *Cucurbita*, wherein said seed can give rise to a plant of the genus *Cucurbita* that is also tolerant or resistant to ToLCNDV. In some embodiments, said seed derives from a plant population, plant, plant part, plant tissue or plant cell of a *C. pepo* plant according to the invention, i.e. said seed is tolerant or resistant to ToLCNDV due to the QTL on LG11 as defined here above conferring said tolerance or resistance. In some embodiments, the plant obtained from said seed is tolerant or resistant to ToLCNDV due to the presence of said QTL on LG11 as defined here above conferring said tolerance or resistance. In some embodiments, the plant obtained from said seed is identified as being tolerant or resistant to ToLCNDV due to the presence of at least one of the following alleles at homozygous state on LG11: allele G of marker SQ-0006678 (SEQ ID NO: 8), allele A of marker SQ-0010844 (SEQ ID NO: 9), and allele C of marker SQ-0000209 (SEQ ID NO: 10). In another embodiment, the plant obtained from said seed is identified as being tolerant or resistant to ToLCNDV due to the presence of allele G of marker SQ-0006678 (SEQ ID NO: 8), allele A of marker SQ-0010844 (SEQ ID NO: 9) and/or allele C of marker SQ-0000209 (SEQ ID NO: 10) at homozygous state on LG11. In another embodiment, the plant obtained from said seed is identified as being tolerant or resistant to ToLCNDV due to the presence of a combination of at least two of the following alleles: allele G of marker SQ-0006678 (SEQ ID NO: 8), allele A of marker SQ-0010844 (SEQ ID NO: 9) and allele C of marker SQ-0000209 (SEQ ID NO: 10) at homozygous state, such as a combination of allele A of marker SQ-0010844 (SEQ ID NO: 9) and allele C of marker SQ-0000209 (SEQ ID NO: 10) at homozygous state.

In some embodiments, said seeds are the deposited seeds TLG (NCIMB 42686). These seeds contain homozygously the QTL on LG11 conferring the tolerance or resistance to ToLCNDV as defined above; they are however distinct on other phenotypic traits such that they do not give rise to a plant variety.

The present invention also provides a tissue culture of a plant population, plant, plant part, plant tissue or plant cell of the genus *Cucurbita*, wherein said tissue culture retains tolerance or resistance to ToLCNDV. In some embodiments, said tissue culture is a tissue culture of a plant population, plant, plant part, plant tissue or plant cell of a *C. pepo* plant according to the invention, i.e. a tissue culture that comprises the QTL on LG11 as defined above conferring the tolerance or resistance to ToLCNDV.

The present invention also provides a progeny derived from the plant of the genus *Cucurbita* as described above, whether produced sexually or asexually, wherein said progeny retains tolerance or resistance to ToLCNDV. In some embodiments, said progeny derives from a plant a *C. pepo* plant according to the invention, i.e. said progeny bears in its genome the QTL associated to tolerance or resistance to ToLCNDV on LG11 as defined here above at homozygous state. In some embodiments, said progeny bears in its genome the QTL associated to tolerance or resistance to ToLCNDV on LG11 as defined here above at heterozygous state.

Thus, the present invention provides methods of isolating a nucleic acid sequence conferring the entire tolerance or resistance to ToLCNDV from a ToLCNDV-resistant plant of the genus *Cucurbita*, plant tissue, or plant cell, comprising:
a) crossing the plant of the genus *Cucurbita* resistant to ToLCNDV as a donor with a suitable plant of the genus *Cucurbita* susceptible, or partially susceptible to ToLCNDV to get offspring plants as a mapping population,
b) challenging said offspring plants with said virus and determining the resistance in said offspring plants, and
c) cloning the nucleic acid sequence. For example, by map-based cloning or association mapping.

One skilled in the art will know how to choose a suitable plant for crossing, and how to clone a nucleic acid sequence by map-based cloning (see, Varshney and Tuberisa, Genomics-assisted crop improvement: Genomics application in crops, Volume 2 of Genomics-assisted Crop Improvement, 2008, Springer, Loze and Wenzel, Molecular marker systems in plant breeding and crop improvement, 2007, Springer, ISBN. 3540740066 9783540740063; Kang, Quantitative genetics, genomics, and plant breeding, 2002, CABI, ISBN 0851996019, 9780851996011, each of which is incorporated herein by reference in its entirety). Such cloned nucleic acid sequence can be transformed into a plant susceptible to ToLCNDV to make it become resistant or tolerant. Methods of plant transformation is well-known in the art, and described separately below. Alternatively, genome fragment comprising said nucleic acid from a donor plant of the genus *Cucurbita* which is resistant to ToLCNDV can be transferred to a recipient plant of the genus *Cucurbita* through any transferring and/or breeding method described separately below.

While the resistance conferring parts are multiple loci in the genome, a QTL (quantitative trait locus) mapping can be applied to determine the parts of the donor plant's genome conferring the ToLCNDV resistance.

Thus, the present invention provides methods of detecting a QTL associated with the resistance to ToLCNDV in a donor plant of the genus *Cucurbita*, comprising:
a) crossing the plant of the genus *Cucurbita* resistant to ToLCNDV as a donor with a suitable plant of the genus *Cucurbita* that is susceptible to said virus to produce offspring plants,
b) challenging one or more said offspring plants with an infective dosage of said virus,
c) quantitatively determining the resistance in said one or more offspring plants,
d) establishing a genetic linkage map that links the observed resistance to the presence of chromosomal markers of said donor plant in said one or more offspring plants, and
e) assigning to a QTL the contiguous markers on said map that are linked to enhanced disease resistance.

Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. level of resistance to virus) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait—these QTLs are often found on different chromosomes. Knowing the number of QTLs that explains variation in the phenotypic trait tells about the genetic architecture of a trait. It may tell that plant resistance to virus of the present invention is controlled by many genes of small effect, or by a few genes of large effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describe cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, The handbook of plant genome mapping: genetic and physical mapping. 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing a gene that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, microsatellites, AFLP, SNP). All differences between two parental genotypes will segregate in a mapping population based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes. This most logical order can be depicted in a linkage map (Paterson, 1996). A group of adjacent or contiguous markers on the linkage map that is associated to a reduced disease incidence and/or a reduced lesion growth rate pinpoints the position of a QTL.

Using QTL mapping analysis, the inventors have been able to identify one QTL conferring the tolerance or resistance to ToLCNDV on linkage group 11 (LG11). Said QTL on LG11 confers tolerance or resistance to ToLCNDV when present at homozygous state.

In some embodiments, said QTL on LG11 is genetically linked to the markers SQ-0006678 (SEQ ID NO: 8), SQ-0010844 (SEQ ID NO: 9) and/or SQ-0000209 (SEQ ID NO: 10).

In some embodiments, said QTL on LG11 conferring the tolerance or resistance to ToLCNDV is located at less than 5 cM, less than 2.5 cM, less than 1 cM, or less than 0.5 cM from markers SQ-0006678 (SEQ ID NO: 8), SQ-0010844 (SEQ ID NO: 9) and/or SQ-0000209 (SEQ ID NO: 10).

In some embodiments, said QTL on LG11 is located in a locus encompassing the markers SQ-0006678 (SEQ ID NO: 8), SQ-0010844 (SEQ ID NO: 9) and/or SQ-0000209 (SEQ ID NO: 10).

In some embodiments, said QTL on LG11 is located within a chromosomal region delimited by marker SQ-0006678 (SEQ ID NO: 8) and marker SQ-0000209 (SEQ ID NO: 10). In some embodiments, said QTL on LG11 is located within a chromosomal region delimited by marker SQ-0010844 (SEQ ID NO: 9) and marker SQ-0000209 (SEQ ID NO: 10). These markers have predictive value for the phenotype of interest, i.e. the tolerance or resistance to ToLCNDV.

The nucleic acid sequence of the QTL of the present invention may be determined by methods known to the skilled person. For instance, a nucleic acid sequence comprising said QTL or a resistance-conferring part thereof may be isolated from a ToLCNDV-resistant donor plant of the genus Cucurbita by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

Such QTL associated with the resistance to ToLCNDV in a donor plant of the genus *Cucurbita* can be transformed into a plant of the genus *Cucurbita* susceptible to ToLCNDV to make it become resistant. Methods of plant transformation is well-known in the art, and described separately below. Alternatively, genome fragment comprising said QTL from a donor plant of the genus *Cucurbita* which is resistant to ToLCNDV can be transferred to a recipient plant of the genus *Cucurbita* through any transferring and/or breeding method described separately below.

In one embodiment, an advanced backcross QTL analysis (AB-QTL) is used to discover the nucleotide sequence or the QTLs responsible for the resistance or susceptibility of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. Theor Appl Genet. 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. A non-limiting exemplary scheme of AB-QTL mapping strategy is shown in FIG. 4. AB-QTL strategy was initially developed and tested in tomato, and has been adapted for use in other crops include rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises of a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL covers usually the complete genome of the donor, or the part of interest.

Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, PLoS Biol.; 2(10):e245).

In one embodiment, when it is not determined that which parts of the donor plant's genome confer the ToLCNDV resistance, complete chromosomes of the donor plant are transferred. For example, the ToLCNDV resistant plant of the genus *Cucurbita* can serve as a male or female parent in a cross pollination to produce resistant offspring plants, wherein by receiving the genomic material form the resistant donor plant, the offspring plants are resistant to ToLCNDV.

Methods of Producing *Cucurbita* Plants Tolerant or Resistant to ToLCNDV

Any *Cucurbita* plant bearing the ToLCNDV resistant QTL on LG11 as defined above can be used to produce more *Cucurbita* plants, especially *C. pepo* plants that are tolerant or resistant to ToLCNDV through plant breeding methods well known to those skilled in the art.

In one embodiment, a ToLCNDV resistant or tolerant plant of the genus *Cucurbita* is used as a donor plant of genetic material which can be transferred to produce a recipient plant which has the transferred genetic material and is also resistant or tolerant to ToLCNDV. Any suitable method known in the art can be applied to transfer genetic material from a donor plant to a recipient plant. In most cases, such genetic material is genomic material.

In one embodiment, the genome of the ToLCNDV resistant plants of the present invention is transferred into a recipient plant. This can be done by crossing the ToLCNDV resistant or tolerant plants to a recipient plant to create a F1 plant. The F1 plant can be further selfed and selected for one, two, three, four, or more generations to give ToLCNDV resistant or tolerant plants.

In another embodiment, at least the tolerance- or resistance-conferring parts of the donor plant's genome, i.e. the QTL on LG11 as defined above, are transferred. This can be done by crossing the ToLCNDV resistant or tolerant plants to a recipient plant to create a F1 plant, followed optionally with one or more backcrosses to one of the parent plants to give ToLCNDV resistant or tolerant plants with the desired genetic background. The progeny resulting from the backcrosses can be further selfed to give ToLCNDV resistant or tolerant plants.

According to the genetic analysis done by the inventors, the nature of the novel tolerance or resistance of the present invention is likely a quantitative recessive locus.

In some embodiments, said QTL conferring the tolerance or resistance to ToLCNDV is located on LG11 and is genetically linked to the markers SQ-0006678 (SEQ ID NO: 8), SQ-0010844 (SEQ ID NO: 9) and/or SQ-0000209 (SEQ ID NO: 10). In some embodiments, said QTL on LG11 conferring the tolerance or resistance to ToLCNDV is located at less than 5 cM, less than 2.5 cM, less than 1 cM, or less than 0.5 cM from markers SQ-0006678 (SEQ ID NO: 8), SQ-0010844 (SEQ ID NO: 9) and/or SQ-0000209 (SEQ ID NO: 10).

In some embodiments, QTL conferring the tolerance or resistance to ToLCNDV is located on LG11 in a locus encompassing the markers SQ-0006678 (SEQ ID NO: 8), SQ-0010844 (SEQ ID NO: 9) and/or SQ-0000209 (SEQ ID NO: 10).

In some embodiments, said QTL conferring the tolerance or resistance to ToLCNDV is located on LG11 within a chromosomal region delimited by marker SQ-0006678 (SEQ ID NO: 8) and marker SQ-0000209 (SEQ ID NO: 10). In some embodiments, said QTL on LG11 is located within a chromosomal region delimited by marker SQ-0010844 (SEQ ID NO: 9) and marker SQ-0000209 (SEQ ID NO: 10).

Thus, in some embodiments, the genome segment comprising said QTL on LG11 can be transferred to a recipient line though breeding methods. As also described elsewhere herein, molecular marker assisted selection can be used to facilitate the breeding.

The invention thus concerns method for the production of Cucurbita plants tolerant or resistant to ToLCNDV, especially commercial plant.

The present invention is indeed also directed to transferring the QTL conferring the tolerance or resistance to ToLCNDV to other Cucurbita varieties, or other species and is useful for producing new types and varieties of ToLCNDV tolerant or resistant Cucurbita plants.

A method or process for the production of a plant having these features may comprise the following steps:
  a) Crossing a plant bearing the ToLCNDV resistant QTL on LG11 as defined above and a Cucurbita plant as a recipient plant, in which the desired phenotype is to be imported or improved; preferably such a Cucurbita plant is susceptible, or less tolerant or resistant, to ToLCNDV;
  b) Selecting a plant in the progeny thus obtained bearing QTL conferring tolerance or resistance to ToLCNDV only when present homozygously,
  c) Optionally, self-pollinating one or several times the plant obtained at step b) and selecting a tolerant or resistant plant in the progeny thus obtained;
wherein markers are used in steps b) and c), for selecting plants bearing QTL conferring tolerance or resistance to ToLCNDV only when present homozygously and/or plants tolerant or resistant to ToLCNDV. The markers are one or more of the markers of the invention, i.e. one or more of the markers SQ-0006678 (SEQ ID NO: 8), SQ-0010844 (SEQ ID NO: 9) and/or SQ-0000209 (SEQ ID NO: 10), and preferably markers SQ-0010844 (SEQ ID NO: 9) and/or marker SQ-0000209 (SEQ ID NO: 10). According to an embodiment, the selection is at least made on the basis of the alleles of markers SQ-0010844 (SEQ ID NO: 9) and/or marker SQ-0000209 (SEQ ID NO: 10). The selection can also be made on the detection of the alleles of all the markers of the invention.

The plant, which is selected at the selection step disclosed above, is selected on the presence of allele G of marker SQ-0006678 (SEQ ID NO: 8), allele A of marker SQ-0010844 (SEQ ID NO: 9), and/or allele C of marker SQ-0000209 (SEQ ID NO: 10). In another embodiment, the plant, which is selected at the selection step disclosed above, is selected on the presence of the allele G of marker SQ-0006678 (SEQ ID NO: 8), allele A of marker SQ-0010844 (SEQ ID NO: 9) and allele C of marker SQ-0000209 (SEQ ID NO: 10). In still another embodiment, the plant, which is selected at the selection step disclosed above, is selected on the presence of at least allele A of marker SQ-0010844 (SEQ ID NO: 9) and allele C of marker SQ-0000209 (SEQ ID NO: 10).

In order to identify plants bearing homozygously or heterozygously the QTL responsible for the tolerance or resistance to ToLCNDV, the presence of the allele linked to the tolerance or resistance is to be detected in combination with the absence of the allele linked to the susceptible parent.

In order to identify plants bearing heterozygously the introgressed sequences, the sole presence of the allele linked to the tolerance or resistance is to be detected.

The method used for allele detection can be based on any technique known by the one skilled in the art allowing the distinction between two different allele of a marker, on a specific chromosome.

A method or process as defined above may advantageously comprises backcrossing steps, preferably after step c), in order to obtain plants having all the characterizing features of C. pepo plants. Consequently, a method or process for the production of a plant having these features may also comprise the following additional steps:
  d) Backcrossing the tolerant plant selected in step c) with a C. pepo plant;
  e) Selecting a plant in the progeny bearing QTL conferring tolerance or resistance to ToLCNDV only when present homozygously,
  f) Self-pollinating the plant obtained at step e), and
  g) Selecting a plant tolerant or resistant to ToLCNDV.

The plant used in step a) can be a plant grown from the deposited seeds NCIMB 42686; it may alternatively be any plant according to the invention, i.e. homozygously tolerant or resistant to ToLCNDV.

Alternatively, the method or process may comprise the following steps:
  a1) Crossing a plant corresponding to the deposited seeds (NCIMB 42686) and a C. pepo plant, in which the desired phenotype is to be imported or improved, thus generating the F1 population;
  a2) Selfing the F1 population to create F2 population;
  b) Selecting tolerant or resistant individuals in the progeny thus obtained;
  c) Optionally self-pollinating one or several times the tolerant plant obtained at step b) and selecting a tolerant or resistant plant in the progeny thus obtained;
  d) Optionally backcrossing the tolerant plant or resistant selected in step b) or c) with C. pepo plant,
  e) Selecting in the progeny a plant bearing sequences linked to the desired phenotype or a plant being tolerant or resistant to ToLCNDV,
  f) Self-pollinating the plant obtained at step e) one or several times, and
  g) Selecting a plant tolerant or resistant to ToLCNDV.

The plant of steps a) or a1) and d) is preferably a plant susceptible to ToLCNDV or a plant less tolerant to ToLCNDV than the plants of the invention.

The plant selected at step b), c) or g) of the preceding methods may be a commercial plant, especially a plant having a bushy type with short internode, early yield and homogeneous fruit color and shape.

Steps d), e) and/or f) may be repeated twice or three times or more, not necessarily with the same C. pepo plant. Said C. pepo plant is preferably a breeding line. This plant is preferably an elite line, used in order to introduce commercially desired traits or desired horticultural traits.

The self-pollination/crossing and backcrossing steps may be carried out in any order and can be intercalated, for example a backcross can be carried out before and after one or several self-pollinations/crossings, and self-pollinations/crossings can be envisaged before and after one or several backcrosses.

Moreover, the methods of the invention are advantageously carried out by using markers as described above for one or more of the selection steps for selecting plants bearing the QTL conferring the tolerance or resistance to ToLCNDV, or for selecting plants having the phenotype of interest. The markers are preferably one or more of the markers of the invention, i.e. one or more of the markers SQ-0006678 (SEQ ID NO: 8), SQ-0010844 (SEQ ID NO: 9) and/or SQ-0000209 (SEQ ID NO: 10), and preferably markers SQ-0010844 (SEQ ID NO: 9) and/or marker SQ-0000209 (SEQ ID NO: 10). According to a preferred embodiment, the selection is at least made on the basis of the alleles of markers SQ-0010844 (SEQ ID NO: 9) and/or marker SQ-0000209 (SEQ ID NO: 10). The selection can also be made on the detection of the alleles of all the markers of the invention.

The plant selected at any one of steps b), e) and/or g) is preferably selected on the presence of the allele G of marker SQ-0006678 (SEQ ID NO: 8), allele A of marker SQ-0010844 (SEQ ID NO: 9), and/or allele C of marker SQ-0000209 (SEQ ID NO: 10). In another preferred embodiment, the plant selected at any one of steps b), e) and/or g) is selected on the presence of the allele G of marker SQ-0006678 (SEQ ID NO: 8), allele A of marker SQ-0010844 (SEQ ID NO: 9) and allele C of marker SQ-0000209 (SEQ ID NO: 10). In still another preferred embodiment, the plant selected at any one of steps b), e) and/or g) is selected on the presence of at least allele A of marker SQ-0010844 (SEQ ID NO: 9) and allele C of marker SQ-0000209 (SEQ ID NO: 10).

The selection of the progeny having the desired phenotype can also be made on conditions of ToLCNDV infection, as disclosed inter alia in example 5 in artificial conditions.

The method used for allele detection can be based on any technique allowing the distinction between two different alleles of a marker, on a specific chromosome locus.

The present invention also concerns any breeding scheme involving as first step crossing a plant grown from one of the deposited seeds (NCIMB 42686).

The present invention also concerns a plant obtained or obtainable by one of the methods described above. Such a plant is indeed a squash (e.g. a *C. pepo*) plant having the desired phenotype according to the invention, i.e. a plant that is tolerant or resistant to ToLCNDV.

The invention also provides a method for producing a hybrid *C. pepo* seed comprising crossing a first cultivar plant parent with a second cultivar plant parent and harvesting the resultant hybrid *C. pepo* seed, wherein both parents are cultivars containing the QTL as defined in the invention in the homozygous or heterozygous state. The hybrid seeds, plant and parts thereof produced by such method are also part of the invention.

In a method for producing a ToLCNDV-resistant or -tolerant plant of the genus *Cucurbita*, protoplast fusion can also be used for the transfer of tolerance- or resistance-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multinucleate cell. The fused cell, that may even be obtained with plant species that cannot be interbred in nature, is tissue cultured into a hybrid plant exhibiting the desirable combination of traits. More specifically, a first protoplast can be obtained from a plant line of the genus *Cucurbita* that is resistant or tolerant to ToLCNDV. For example, a protoplast from a ToLCNDV-resistant or -tolerant squash line may be used. A second protoplast can be obtained from a susceptible second plant line, optionally from another plant species or variety, such as from the same plant species or variety, that comprises commercially desirable characteristics, such as, but not limited to disease resistance, insect resistance, valuable fruit characteristics, etc. The protoplasts are then fused using traditional protoplast fusion procedures, which are known in the art to produce the cross.

Alternatively, embryo rescue may be employed in the transfer of tolerance- or resistance-conferring genomic material from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, In vitro culture of higher plants, Springer, ISBN 079235267x, 9780792352679, which is incorporated herein by reference in its entirety).

In addition, in one embodiment, a method for producing a ToLCNDV-resistant or -tolerant plant of the genus *Cucurbita* comprises grafting a susceptible recipient plant of the genus *Cucurbita* onto resistant rootstocks of ToLCNDV resistant or tolerant plants, which is proved to be an effective methodology developed for intensive cultivation in the Far East (Lee and Oda, 2003, Grafting of herbaceous vegetable and ornamental crops, Hort. Rev. 28:61-124).

In some embodiments, the recipient plant is a squash plant, such as a *C. pepo* plant, or any other cucurbit plant that can hybridize with the ToLCNDV resistant or tolerant plant of the invention.

In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, production of specific biofuels, increased food production, improved food quality, etc. Additional examples of agronomically important traits includes pest resistance, vigor, development time (time to harvest), enhanced nutrient content, novel growth patterns, flavors or colors, salt, heat, drought and cold tolerance, and the like. Agronomically important traits do not include selectable marker genes (e.g., genes encoding herbicide or antibiotic resistance used only to facilitate detection or selection of transformed cells), hormone biosynthesis genes leading to the production of a plant hormone (e.g., auxins, gibberellins, cytokinins, abscisic acid and ethylene that are used only for selection), or reporter genes (e.g. luciferase, β-glucuronidase, chloramphenicol acetyl transferase (CAT, etc.).

Other agronomically important traits include resistance to biotic and/or abiotic stresses. As used herein, the phrase "biotic stress" or "biotic pressure" refers to a situation where damage is done to plants by other living organisms, such as bacteria, viruses, fungi, parasites, insects, weeds, animals and human. As used herein, the phrase "abiotic stress" or "abiotic pressure" refers to the negative impact of non-living factors on plants in a specific environment. The non-living variable must influence the environment beyond its normal range of variation to adversely affect the population performance or individual physiology of plants in a significant way. Non-limiting examples of stressors are high winds, extreme temperatures, drought, flood, and other natural disasters, such as tornados and wildfires. For example, the plant lines developed using the genetic materials and methods of the present invention can also include resistance to ToLCNDV due to one or more different loci other than the QTL on LG11 as defined here above; resistance to other types of geminiviruses other than ToLCNDV; and/or resistance to other pathogens (e.g., fungal plant pathogens, oomycetes, bacterial plant pathogens, insects et al.).

A list of popular North America squash cultivars with various agronomically important traits can be found in the Cucurbit Breeding database of North Carolina State University (Wessel-Beaver et al., Vegetable Cultivar Descriptions for North America, Squash, Retrieved on Apr. 21, 2010, incorporated by reference in its entirety).

The recipient line will have one or more preferred cucurbit traits. These traits include, but are not limited to, resistance/tolerance to pathogens, such as to *Alternaria* leaf spot (*Alternaria Cucumerina*), Angularlsp spot (*Pseudomonas syringae*), *Colletotrichum orbiculare*, *Edwinia tracheiphila*, Bean Yellow Mosaic Virus, Cucumber Mosaic Virus, downy mildew (*Pseudoperonospora cubensis*), fruit rot (*Rhizoctonia solani*), Fusarium wilt (*Fusarium solani* f. *cucurbitae*), gummy stem blight, melon mosaic virus, *Phyllosticta cucurbitacearum*, *Phytophthora* (*Phytophthora capsici*), powdery mildew (*Erysiphe cichoracearum*), potyviruses (e.g., malva vein clearing potyvirus, potato virus Y, turnip mosaic virus, plum Pox Potyvirus, tulip breaking virus, papaya ringspot virus, apium virus Y, bidens mottle virus, celery mosaic virus, commelina mosaic virus, and tradscantia mosaic virus), seedling blight (*Pythum aphanidermatum, Pythum irregulare, Pythum ultimum, Rhizoctonia solani*), Septoria (*Septoria cucurbitacearum*), Stemphylium (*Stemphylium cucurbitacearum*), target leaf spot (*Corynespora cassiicola*), tobacco ringspot virus, and tomato ringspot virus; resistance/tolerance to insects such as to Atlantic spider mite, banded cucumber beetle, brown wheat mite, darkling ground beetle, desert spider mite, green peach aphid, leaf hoppers, melon aphid, pacific spider mite, spotted cucumber beetle, squash bug, squash vine borer, two spotted spider mite, western corn root worm, western spotted cucumber beetle, white fly, root-knot nematode; specific flower-fruit related traits, such as traits related to abscission, bitterness, blossom scar, fruit skin pattern, flesh color, flesh thickness, fruit diameter, fruit length, fruit rib, fruit shape, seed cavity color, fruit skin texture, spine color and fruit weight; specific type of plant growth habit; certain genetic loci, such as 6-phosphogluconate dehydrogenase loci, glucosephosphate isomerase loci, glutahtione reductase loci, isocitrate dehydrogenase loci, malic dehydrogenase loci, monosephosphate isomerase loci, peptidase with leucyl-alanine loci, peptidase loci, phosphoglucomutase loci, shikimate dehydrogenase loci); certain specific morphological traits, such as size/type of the blossom end fruit shape, size/type of cavity diameter, size/type of the blossom scar, ease of peduncle separation from fruit, ease of seed separation from flesh, external aroma, flesh color intensity, flesh flavor, flesh moisture, flower color, fruit skin corking, fruit skin glossiness, fruit splitting, fruit stem color, fruit stripes on blossom end, fruit volume, fruit width, internal aroma, internal color of skin, internode length, leaf color, leaf lobes, leaf shape, leaf size, number of fruits harvested per plant, number of seeds per fruit, seed coat color, seed shape, seed size, skin hardness of fruit), or certain preferred phenological traits, such as a desired time of maturity (based on accumulated heat units, days after planting, and/or day length), desired production related traits (e.g., 100 seed weight, flesh dry matter percent, fruit storage ability, fruit weight), and/or desired stress related traits (e.g., tolerance to drought, tolerance to salt, tolerance to low and high temperatures).

As mentioned above, the tolerance or resistance in the ToLCNDV tolerant/resistant plant provided by the present invention is likely due to a QTL in the genome based on genetic analysis. In some embodiments, said QTL conferring the tolerance or resistance is located on LG11 and is genetically linked to the markers SQ-0006678 (SEQ ID NO: 8), SQ-0010844 (SEQ ID NO: 9) and/or SQ-0000209 (SEQ ID NO: 10) as defined here above. In some embodiments, said QTL conferring the tolerance or resistance is located on LG11 in a locus encompassing the markers SQ-0006678 (SEQ ID NO: 8), SQ-0010844 (SEQ ID NO: 9) and/or SQ-0000209 (SEQ ID NO: 10). In some embodiments, said QTL conferring the tolerance or resistance is located on LG11 within a chromosomal region delimited by marker SQ-0006678 (SEQ ID NO: 8) and marker SQ-0000209 (SEQ ID NO: 10), and preferably within a chromosomal region delimited by marker SQ-0010844 (SEQ ID NO: 9) and marker SQ-0000209 (SEQ ID NO: 10).

One skilled in the art will know how to clone said QTL on LG11 using the ToLCNDV resistant or tolerant plants of the present invention. For example, one skilled in the art will be able to choose a suitable plant for crossing, generate a mapping population, and isolate polynucleotide of the gene responsible for the tolerance or resistance located in said QTL on LG11 by map-based cloning or any other suitable methods (see, Varshney and Tuberisa, *Genomics-assisted crop improvement: Genomics application in crops, Volume 2 of Genomics-assisted Crop Improvement*, 2008, Springer, Loze and Wenzel, *Molecular marker systems in plant breeding and crop improvement*, 2007, Springer, ISBN. 3540740066 9783540740063; Kang, *Quantitative genetics, genomics, and plant breeding*, 2002, CABI, ISBN 0851996019, 9780851996011, each of which is incorporated herein by reference in its entirety). Such isolated polynucleotide sequence can be transferred into a recipient plant susceptible to ToLCNDV through any breeding method described separately below, to make a new line that is resistant or tolerant.

The isolated polynucleotide of gene responsible for the tolerance or resistance located in said QTL on LG11 can be used in many aspects. In one embodiment, the nucleic acid sequence of said isolated gene, or any function variant thereof, can be expressed in other plant species that are susceptible to ToLCNDV, and wherein said species cannot hybridize with cucurbit plants of the present invention. For example, said species is other *Cucurbitae* species, such as melon, cucumber, watermelon. In other embodiment, said isolated gene, or fragment thereof can be used as probe to identify and/or isolate homologous genes in other plants.

Molecular Markers Closely Linked to Tolerance or Resistance QTL on LG11

The inventors of the present invention also provide molecular markers that are tightly linked to the ToLCNDV tolerant/resistant locus in the plants of the present invention.

At least three SNP marker, i.e. the markers SQ-0006678 (SEQ ID NO: 8), SQ-0010844 (SEQ ID NO: 9) and/or SQ-0000209 (SEQ ID NO: 10), were found to be closely linked (less than 5 cM) to the ToLCNDV tolerant/resistant locus on LG11.

Molecular markers have proven to be of great value for increasing the speed and efficiency of plant breeding. Most traits of agronomic value, e.g. pest resistance, yield and the like, are difficult to measure, often requiring a full growth season and statistical analysis of field trial results. Interpretation of the data can be obscured or confused by environmental variables. Occasionally it has been possible for breeders to make use of conventional markers such as flower color which could be readily followed through the breeding process. If the desired QTL is linked closely enough to a conventional marker, the likelihood of recombination occurring between them is sufficiently low that the QTL and the marker co-segregate throughout a series of crosses. The marker becomes, in effect, a surrogate for the QTL itself. Prior to the advent of molecular markers, the opportunities for carrying out marker-linked breeding were severely limited by the lack of suitable markers mapping sufficiently close to the desired trait. Map distance is simply a function of recombination frequency between two markers, QTLs or markers and QTLs. Consequently, if a marker and a QTL map too far apart, too much recombination will occur during a series of crosses or self-pollinations such that the marker becomes no longer associated with the QTL. Having a wide selection of molecular markers available throughout the genetic map provides breeders the means to follow almost any desired trait through a series of crosses, by measuring the presence or absence of a marker linked to the QTL which affects that trait. The primary obstacle is the initial step of identifying a linkage between a marker and a QTL affecting the desired trait.

The inventors of the present invention identified such molecular markers that are tightly linked to the tolerance or resistance to ToLCNDV, which brings huge advantage in the breeding program targeting improve the tolerance or resistance to ToLCNDV in cucurbit plants. Molecular markers provide two additional operational advantages. First, since they exist as features of the plant DNA itself, they can be detected soon after germination, for example by analysis of leaf DNA of seedlings. Selection for plants carrying the marker can be performed at the seedling stage, thereby saving the space and energy formerly needed to grow large numbers of plants to maturity. Second, molecular markers do not depend on gene expression for detection. Their use is unlikely to lead to misleading results, such as can occur when environmental or other variables modify expression of conventional marker genes.

More molecular markers can be developed by using the ToLCNDV resistant or tolerant plants of the present invention. In general, as the map distance (expressed by the unit cM) between a molecular marker and a gene of interest becomes shorter, the marker and the gene are more closely localized to each other, and more likely to be inherited simultaneously; thus such markers are more useful. Methods of developing molecular markers are well known to one of ordinary skill in the art. The markers can be bi-allelic dominant, bi-allelic co-dominant, and/or multi-allelic co-dominant. The types of molecular markers that can be developed include, but are not limited to, restriction fragment length polymorphisms (RFLPs), isozyme markers, allele specific hybridization (ASH), amplified variable sequences of plant genome, self-sustained sequence replication, simple sequence repeat (SSR), single base-pair change (single nucleotide polymorphism, SNP), random amplification of polymorphic DNA (RAPDs), SSCPs (single stranded conformation polymorphisms); amplified fragment length polymorphisms (AFLPs) and microsatellites DNA.

Methods of developing molecular markers and their applications are described by Avise (Molecular markers, natural history, and evolution, Publisher: Sinauer Associates, 2004, ISBN0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety.

Thus, the present invention provides at least one molecular marker that is closely linked to the tolerance or resistance locus of the ToLCNDV tolerant/resistant plants of the present invention. In some embodiments, said molecular marker is chosen from the group consisting of marker SQ-0006678 (SEQ ID NO: 8), marker SQ-0010844 (SEQ ID NO: 9), marker SQ-0000209 (SEQ ID NO: 10), and any other markers within a chromosomal region delimited by marker SQ-0006678 (SEQ ID NO: 8) and marker SQ-0000209 (SEQ ID NO: 10), or a chromosomal region delimited by marker SQ-0010844 (SEQ ID NO: 9) and marker SQ-0000209 (SEQ ID NO: 10). In some embodiments, said molecular marker is marker SQ-0010844 (SEQ ID NO: 9) and/or marker SQ-0000209 (SEQ ID NO: 10).

The molecular markers of the present invention are closely linked to the ToLCNDV resistant locus. As used herein, the phrase "closely linked" or "tightly linked" refers to the situation wherein the genetic distance between the molecular marker and the ToLCNDV resistant locus is less than 5 centimorgan (cM). For example, the genetic distance between the marker and the QTL is about 4.9 cM, 4.8 cM, 4.7 cM, 4.6 cM, 4.5 cM, 4.4 cM, 4.3 cM, 4.2 cM, 4.1 cM, 4.0 cM, about 3.9 cM, 3.8 cM, 3.7 cM, 3.6 cM, 3.5 cM, 3.4 cM, 3.3 cM, 3.2 cM, 3.1 cM, 3.0 cM, about 2.9 cM, 2.8 cM, 2.7 cM, 2.6 cM, 2.5 cM, 2.4 cM, 2.3 cM, 2.2 cM, 2.1 cM, 2.0 cM, about 1.9 cM, about 1.8 cM, about 1.7 cM, about 1.6 cM, about 1.5 cM, about 1.4 cM, about 1.3 cM, about 1.2 cM, about 1.1 cM, about 1.0 cM, about 0.9 cM, about 0.8 cM, about 0.7 cM, about 0.6 cM, about 0.5 cM, about 0.4 cM, about 0.3 cM, about 0.2 cM, about 0.1 cM, or less than 0.1 cM.

The molecular markers identified herein can be used in many aspects of the present invention. For example, the molecular markers can be used to assist a breeding program wherein the goal is to transfer ToLCNDV tolerance or resistance in the cucurbit lines of the present invention to other cucurbit lines. Detailed methods of molecular marker assistant selection/breeding is described by Wenzel (Molecular Marker Systems in Plant Breeding and Crop Improvement, Volume 55 of Biotechnology in Agriculture and Forestry, Publisher: Springer, 2007, ISBN 3540740066, 9783540740063), Xu (Molecular Plant Breeding, CABI, February 2010, ISBN 1845933923, 9781845933920), and Kang (Quantitative genetics, genomics, and plant breeding, CABI Publishing Series, 2002, ISBN 0851996019, 9780851996011), each of which is incorporated by reference in its entirety.

Breeding Methods

Open-Pollinated Populations. The improvement of open-pollinated populations of such crops as squash, rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed "en masse" by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, Principles of Plant Breeding, John Wiley & Sons, Inc. (1960); Simmonds, Principles of Crop Improvement, Longman Group Limited (1979); Hallauer and Miranda, Quantitative Genetics in Maize Breeding, Iowa State University Press (1981); and, Jensen, Plant Breeding Methodology, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the production of both the parental lines and the hybrids which result from crossing those lines. For a detailed discussion of the hybrid production process, see, e.g., Wright, Commercial Hybrid Seed Production 8:161-176, In Hybridization of Crop Plants.

Bulk Segregation Analysis (BAS). BAS, a.k.a. bulked segregation analysis, or bulk segregant analysis, is a method is described by Michelmore et al. (Michelmore et al., 1991, Proceedings of the National Academy of Sciences, USA, 99:9828-9832) and Quarrie et al. (Quarrie et al., 1999, Journal of Experimental Botany, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

Accordingly, the present invention is also directed to the use of a *C. pepo* plant tolerant or resistant to ToLCNDV as defined above, as a breeding partner in a breeding program for obtaining *C. pepo* plants tolerant or resistant ToLCNDV. Indeed, such a *C. pepo* plant tolerant or resistant to ToLCNDV harbors in its genome one QTL on LG11 as defined here above conferring said tolerance or resistance. In an embodiment, such a *C. pepo* plant tolerant or resistant to ToLCNDV harbors in its genome at least one or more of the following alleles: allele G of marker SQ-0006678 (SEQ ID NO: 8), allele A of marker SQ-0010844 (SEQ ID NO: 9), and/or allele C of marker SQ-0000209 (SEQ ID NO: 10). In another embodiment, such a *C. pepo* plant tolerant or resistant to ToLCNDV harbors in its genome allele G of marker SQ-0006678 (SEQ ID NO: 8), allele A of marker SQ-0010844 (SEQ ID NO: 9) and allele C of marker SQ-0000209 (SEQ ID NO: 10). In still another embodiment, such a *C. pepo* plant tolerant or resistant to ToLCNDV harbors in its genome at least allele A of marker SQ-0010844 (SEQ ID NO: 9) and allele C of marker SQ-0000209 (SEQ ID NO: 10).

By crossing this plant with susceptible or less tolerant plants, it is thus possible to transfer this QTL. A plant according to the invention can thus be used as a breeding partner for introgressing the QTL on LG11 conferring the desired phenotype. In some embodiments, a plant according to the invention can be used as a breeding partner for introgressing the QTL on LG11 as defined above conferring the desired phenotype. In some embodiments, a plant according to the invention can be used as a breeding partner for introgressing at least one or more of the following alleles on LG11: allele G of marker SQ-0006678 (SEQ ID NO: 8), allele A of marker SQ-0010844 (SEQ ID NO: 9), and/or allele C of marker SQ-0000209 (SEQ ID NO: 10). In some embodiments, a plant according to the invention can be used as a breeding partner for introgressing allele G of marker SQ-0006678 (SEQ ID NO: 8), allele A of marker SQ-0010844 (SEQ ID NO: 9) and allele C of marker SQ-0000209 (SEQ ID NO: 10) on LG11. In some embodiments, a plant according to the invention can be used as a breeding partner for introgressing at least allele A of marker SQ-0010844 (SEQ ID NO: 9) and allele C of marker SQ-0000209 (SEQ ID NO: 10) on LG11.

The invention is also directed to the same use with plants or seeds of plant TLG as deposited at NCIMB under accession number 42686. Said plants are also suitable as introgression partners in a breeding program aiming at conferring the desired phenotype to a *C. pepo* plant or germplasm.

In such a breeding program, the selection of the progeny displaying the desired phenotype, or bearing QTL linked to the desired phenotype, can advantageously be carried out on the basis of the allele of the marker disclosed here above. The progeny is selected on the presence of one or more of the following alleles: allele G of marker SQ-0006678 (SEQ ID NO: 8), allele A of marker SQ-0010844 (SEQ ID NO: 9), and/or allele C of marker SQ-0000209 (SEQ ID NO: 10) on LG11. In some embodiments, the progeny is selected on the presence of all of allele G of marker SQ-0006678 (SEQ ID NO: 8), allele A of marker SQ-0010844 (SEQ ID NO: 9) and allele C of marker SQ-0000209 (SEQ ID NO: 10) on LG11. In some embodiments, the progeny is selected on the presence of at least allele A of marker SQ-0010844 (SEQ ID NO: 9) and allele C of marker SQ-0000209 (SEQ ID NO: 10) on LG11.

The selection of the progeny having the desired phenotype can also be made on conditions of pathogens infestation, as disclosed inter alia in the section ToLCNDV test of the examples.

A plant according to the invention, or as deposited under accession number NCIMB 42686, is thus particularly valuable in a marker-assisted selection program for obtaining commercial *C. pepo* lines and varieties tolerant or resistant to ToLCNDV. The invention is also directed to the use of said plants in a program aiming at identifying, sequencing and/or cloning the genes conferring the desired phenotype, i.e. tolerant or resistant to ToLCNDV.

It should be understood that the examples and embodiments described herein are for illustrative purposes only and that various modifications or changes in light thereof will be suggested to persons skilled in the art and are to be included within the spirit and purview of this application.

DEPOSIT INFORMATION

A representative sample of seeds from the *C. pepo* plant according to the invention (i.e. seeds from TLG plant) has been deposited by HM. Clause, S. A., Rue Louis Saillant, Z. I. La Motte, BP83, 26802 Portes-lès-Valence cedex, France, under the authorization of the owner of the present invention (i.e., Vilmorin & Cie), pursuant to, and in satisfaction of, the requirements of the Budapest Treaty on the International Recognition of the Deposit of Microorganisms for the Purposes of Patent Procedure (the "Budapest Treaty") with the National Collection of Industrial, Food and Marine Bacteria (NCIMB), Ferguson Building, Craibstone Estate, Busksburn, Aberdeen, Scotland, AB21 9YA, United Kingdom, on Nov. 4, 2016, under accession number 42686.

A deposit of the TLG seeds is maintained by HM. Clause, S. A., Rue Louis Saillant, Z. I. La Motte, BP83, 26802 Portes-lès-Valence cedex, France, under the authorization of the owner of the present invention (i.e., Vilmorin & Cie).

To satisfy the enablement requirements of 35 U.S.C. 112, and to certify that the deposit of the seeds of the present invention meets the criteria set forth in 37 CFR 1.801-1.809, Applicants hereby make the following statements regarding the deposit of the resistant germplasm:

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer; and
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to the deposit.

EXAMPLES

Example 1. ToLCNDV Characterization in Squash

In the first year, two samples of squash having fruit and distortion have been received from Spain. Regular ELISA tests identified first the presence of Cucumber Mosaic Virus (CMV) and Cucurbit Yellowing Stunting Disorder Virus (CYSDV). In a second phase, strategic pathogens commonly present in the Mediterranean area have been tested in these two samples, and the presence of the Begomovirus called Squash Leaf Curl Virus (SLCV) together with another virus closed to the Begomovirus cluster has been detected.

Six more squash samples coming from Spain's farmers have been further tested for the presence of this new virus, and the presence of this new Begomovirus has been confirmed in all the six samples. After phylogenetic analysis, it has been demonstrated that this new virus is not distinguishable from Tomato Leaf Curl New Dehli Virus that is known to infect tomatoes.

Example 2. PCR Detection of Begomoviruses

Total DNA was extracted from 0.05 g of plant tissues (leaf or fruit) using the DNeasy plant mini kit from Qiagen GmBH according to the manufacturer instructions. The forward primer and the reverse primer for detecting begomoviruses have respectively the sequences 5'-GGCTGT-GAAGGCCCATGTAA-3' (SEQ ID NO: 4) and 5'-ATG-GATTCACGCACAGGGG-3' (SEQ ID NO: 5). PCR reactions were performed in a final volume of 22 µl containing 2 µl of genomic DNA, 4 µM of each primer and 1 unit of Taq Diamond DNA polymerase (Eurogentec). The thermal cycling conditions comprised an initial denaturation step at 95° C. for 15 min, 35 cycles at 94° C. for 30 s and 60° C. for 30 s and 72° C. for 1 min, and an elongation step at 72° C. for 7 min. The length of the amplified DNA fragment was then controlled by electrophoresis on an agarose gel 1.5% TAE 1×. The expected length of the fragment is 981 bp. The DNA fragment amplified was sequenced using the Sanger method. This step is done by GATCH Biotech Company. The sequences obtained are corrected using Seqtrace software and the sequences alignment and phylogenetic trees building were done using MEGA software. Sequencing of the DNA fragment allowed to identify the presence or absence of the ToLCNDV.

Since this PCR detection protocol was not specific for detecting the ToLCNDV, and implies to sequence the amplified DNA fragment for identifying the ToLCNDV, the inventors developed a novel PCR protocol in order to fasten ToLCNDV identification without the sequencing step (see Example 3).

Example 3. PCR Detection of ToLCNDV

Total DNA was extracted from 0.05 g of plant tissues (leaf or fruit) using the DNeasy plant mini kit from Qiagen GmBH according to the manufacturer instructions. The forward primer and the reverse primer for detecting the ToLCNDV (i.e. primers for amplifying the sequence SEQ ID NO: 3) have respectively the sequences 5'-TTGGATC-CATGGCGAAGCGACCA-3' (SEQ ID NO: 6) and 5'-AAGAGCTCTTAATTTGTGACCGA-3' (SEQ ID NO: 7). PCR reactions were performed in a final volume of 20 µl containing 2 µl of genomic DNA, 4 µM of each primer and 1 unit of Taq Diamond DNA polymerase (Eurogentec). The thermal cycling conditions comprised an initial denaturation step at 95° C. for 15 min, 35 cycles at 94° C. for 30 s and 40° C. for 30 seconds and 72° C. for 1 minute, and an elongation step at 72° C. for 7 minutes. The length of the amplified DNA fragment was then controlled by electrophoresis on an agarose gel 1.5% TAE 1×. The expected length of the fragment is 750 bp.

Example 4. Detection of ToLCNDV Resistant Sources in Open Field Conditions

A field trial in Spain station was set-up during the summer of the second year, with the aim to evaluate some *Cucurbita* germplasm in natural infection conditions.

Different *Cucurbita* species (*Cucurbita pepo, Cucurbita moschata, Cucurbita ecuadorensis, Cucurbita okeechobeensis, Cucurbita foetidissima, Cucurbita ficifolia, Cucurbita pedatifolia*) and other Cucurbit accession, such as *Luffa* sp., *Lagenaria* sp. have been tested. The trial was made of four replications of 10 plants per accession, sown on august 21st and each replication was planted on September, 2nd in a plastic tunnel (total four plastic tunnels). Plantation was based on a completely randomized bloc design. Tunnels borders were opened and no chemicals were applied in order to facilitate whiteflies infection and ToLCNDV development. Three evaluations were done on September 23rd, October 6$^{th}$ and October 15$^{th}$ based on a qualitative scale: 0=no foliar symptom; 1=foliar symptom (from light mosaic to leaf curling). Each plant was rated this way. Leaf samples were collected on symptomatic and resistant plants in order to monitor disease infection and to be sure that the trial was not cross-contaminated with another virus.

First evaluation in the field trial first demonstrated that ToLCNDV was the only virus detected and that the infection rate and coverage of the trial were good.

Raw data based on the percentage of infected plants (four repetitions summed) shows a black or white response, even at the first evaluation. For some entries (MOSCHATA 1, *Luffa* special long, Ns), no symptom recovery but a late disease expression has been observed. Resistant entries did not show any symptom at any evaluation date (see FIG. 1).

Among *Cucurbita moschata* group, Nigerian did not perform good regarding ToLCNDV infection in open field condition. Menina Portugal, Menina Brasileira, MOSCHATA 1 and MOSCHATA 2 are *Cucurbita moschata* entries, already used in breeding programs and among them, only Menina Portugal and Menina Brasileira showed no symptom during the trial. Leaf samples were collected and no ToLCNDV was detected with molecular tools. This accession seems to be immune to ToLCNDV. Menina brasileirinha, described as whitefly resistant, also showed some ToLCNDV resistance but did not perform as Menina Brasileira or Menina Portugal.

Among other *Cucurbita* species, only *C. pedatifolia* (PI442290) and *Luffa* accessions did not show any symptoms, but ToLCNDV was detected on leaf tissue, suggesting that they have a different resistance mechanism compared to the *C. moschata* accession Menina Portugal.

Example 5. Detection of ToLCNDV Resistant Sources in Artificial Pathological Test To confirm that the above identified accessions were resistant, the inventors decided to test them with an artificial test that has been developed internally. They also tested one *C. moschata* Nigerian Local accession, i.e. the "Nigerian" accession.

5.1. Virus Isolation and Maintenance

The virus was isolated from symptomatic squash hybrid (*C. pepo*) plants during the squash-growing season in Spain. Infected leaves were stored in a plastic bag at −80° C. to be used as the source of successive mechanical inoculations. ELISA, PCR and sequencing were done to eliminate possible contamination with other viruses and to obtain a ToLCNDV isolate for the artificial pathological test.

5.2. Mechanical Inoculation

One melon susceptible hybrid was used to propagate the inoculum. The inoculum was made by grinding 1 g of infected leaves with 4 ml of a 0.03M $Na_2HPO_4$ buffer containing 0.2% sodium diethyldithiocarbamate with carborundum (7.5%) and activated carbon (10%). Seedlings with first leaf not yet emerged were inoculated on both cotyledons.

A second inoculation, based on the same process, is done one week later on the first leaf. The test is conducted in growth chamber under a photoperiod of 14 h of daylight at 25° C. and 10 h of night at 20° C.

5.3. Symptoms Evaluation

The evaluation is performed once a week during 3 to 4 weeks after inoculation. One susceptible control (i.e. the Victoria variety) was included in each tray to check for infection rate. Evaluation is done on an ordinal scale: 1: Plant stunting with severe reduction of apical leaves; 3:

growth reduction, severe vein banding on young leaves; 5: slight symptoms on apical leaves; 7: slight symptoms on intermediate leaves but no symptom on apex and 9: no symptom at all.

5.4. Results

Several scorings had to be done because of symptoms evolution; at least the susceptible check (cv. Victoria) was fully symptomatic only 3 weeks after inoculation. The obtained results confirmed that *C. moschata* Menina Portugal is resistant with a scoring of 9 (FIG. 2). The results also showed that the Nigerian accession is resistant to ToLCNDV (FIG. 3).

Example 6. Determination of the Resistance to ToLCNDV in *C. moschata* Menina Portugal In order to identify the genetic determinism of the resistance present in *C. moschata* Menina Portugal, a cross between the susceptible Tarmino variety and Menina Portugal has been done. The F1 progenies then have been selfed to obtain an F2 population. The F2 distribution has been analyzed with JMP software and R software and khi$^2$ tests has been done with a contingency table in order to compare observed and expected results. The results obtained suggest a recessive inheritance (Table 2).

More particularly, the following three populations have been used to map QTL(s) controlling the resistance to ToLCNDV:

A F1 population called "BRV" obtained from the cross between the resistant source *C. moschata* Menina Brasileira and the susceptible line "DIVA", One BC1F2 population called "TLG BC1". This population has been obtained as follow. The resistant source *C. moschata* Menina Portugal has been crossed with the susceptible line "Tarmino" to obtain a F1 population called AW026, then plants of this F1 population have been selfed to obtain the F2 population. A pathological evaluation of the F2 plants was done using the protocol disclosed in Example 5, and resistant plants were selected to the back-crossed with the recurrent parent "DGN" to obtain the BC1 population. Then plants of the BC1 population were selfed to obtain the BC1F2 population.

One BC2F2 population is called "TLG BC2". This population has been obtained as follow. The resistant source *C. moschata* Menina Portugal has been crossed with the susceptible line "Tarmino" to obtain a F1 population. Plants of the F1 population were backcrossed with the recurrent parent "Tarmino" to obtain a BC1 population. Plants of the

TABLE 2

Distribution of the F2 progenies (WTAJ07) derived from the cross Tarmino × Menina Portugal and compared to the susceptible control (Victoria).

| progeny | number of plants | Observed phenotype | | | Observed ratio (R:S) | Expected ratio (R:S) | $\chi^2$ p-value |
|---|---|---|---|---|---|---|---|
| | | Resistant (scores 7 + 9) | Intermediate (score 5) | susceptible (scores 1 + 3) | | | |
| Victoria (Susceptible control) | 38 | | 1 | 37 | 0:37 | 0:38 | na |
| Menina Portugal | 41 | 41 | | | 41:0 | 41:0 | na |
| Tarmino | 45 | | | 45 | 0:45 | 0:45 | na |
| F2 named WTAJ07 | 76 | 18 | 6 | 52 | 18:52 | 19:60 | 0.03795* | p-value with a * are significatively different ($\alpha$ = 5%)
na = non applicable The distribution of the scores were compared to the expected ratio (khi$^2$ test) according to a recessive gene inheritance. The p-value is in every case significant, meaning that this model suits the observed data.

Example 7. Breeding of *Cucurbita Pepo* Varieties Resistant to ToLCNDV

In preliminary trials in Spain with natural infection of ToLCNDV, the inventors had a number of varieties of *Cucurbita pepo*, as well as several varieties of *Cucurbita moschata*. The results were that all the *C. pepo* varieties were susceptible, whereas some of the *C. moschata* varieties were resistant, as shown in examples 4 and 5. More particularly, *C. moschata* Menina Portugal, *C. moschata* Nigerian, and *C. moschata* Brasileira are resistant to ToLCNDV. Based on the results of these studies, we concluded that these three *C. moschata* accessions are good sources of resistance for breeding and it was, therefore, chosen as a donor of resistance to ToLCNDV-caused viral diseases. The breeding scheme is summarized in FIG. 5.

Several germplasms were created in order to develop a molecular marker map and develop resistance to viruses, which can be used in the process of transferring ToLCNDV resistance from these *C. moschata* accessions to *C. pepo*.

BC1 population have then been selfed to obtain a BC1F2 population. A pathological evaluation of the BC1F2 plants was done using the protocol disclosed in Example 5, and resistant plants were selected to the backcrossed with the recurrent parent "DGN" to obtain the BC2 population. Then plants of the BC2 population were selfed to obtain the BC2F2 population.

These 3 populations were tested for their resistance to ToLCNDV according to the protocol disclosed in Example 5, and they were phenotyped in Spain at different time after inoculation, e.g. from 26 days post inoculation to 65 days post inoculation for the BRV population, or at 36 days post inoculation for the "TLG BC1" and "TLG BC2" populations.

These populations have then been genotyped to identity the QTL(s) responsible for the resistance to ToLCNDV. A total of 48 SNP markers were selected for an initial screening of the populations. KASPar™ primers were designed using PrimerPicker™ tool in KLIMS™ (KBioscience Laboratory Management System) by providing DNA sequences with SNPs. Three primers, A1 (Allele specific primer 1), A2 (Allele specific primer 2), and C (common reverse primer) were designed for each SNP sequence based on KASPar™ chemistry.

An assay mix of each KASPar™ reaction was prepared as in the KASPar™ SNP Genotyping System v2.0. The final reaction volume was 2 μL, per reaction, including 1 μL DNA template (5 ng/μL), 0.98 μL Kaspar Reaction mix v4, 0.014 μL Assay mix (6:6:15 ratio of primers A1:A2:C). The assay was carried out in 1536-well format. The thermocycle conditions used during the assay were according to the manufacturer's instructions: 94° C. for 15 minutes; 10 cycles of 94° C. for 20 seconds, 65° C. for 60 seconds with −0.8° C. per cycle; and 26 cycles of 94° C. for 20 seconds, 57° C. for 60 seconds. PCR plates were centrifuged, and allele-specific FAM and VIC intensities were read on a PHERAstar® spectrofluorometer (BMG LaBTech) at room temperature. Data were directly loaded and analyzed on KLIMS™ using Kluster Caller™

Analysis of variance (ANOVA) was performed for all data using the GLM procedure of SAS Institute (1999). Linkage analysis identified a single major QTL on chromosome 11 which is defined by set of markers significantly linked to resistance to ToLCNDV. The list of associated markers and their significance are summarized in Table 3. The SNPs were physically mapped to the public available squash genomic map v3.2 (https://cucurbigene.upv.es/genome-v3.2/).

TABLE 3

SNPs linked to the resistance to ToLCNDV.

| Population | Variable | Marker | Physical position on CP32_scaffold000045 | R allele/ S allele | P-value | $R^2$ |
|---|---|---|---|---|---|---|
| BRV | 29 dpi | SQ-0010844 | 1004822 | A/C | 4.10E−07 | 36.0% |
|  |  | SQ-0000209 | 1020668 | G/T | 4.10E−07 | 36.0% |
|  |  | SQ-0006678 | 837806 | G/A | 5.73E−06 | 30.6% |
|  | 36 dpi | SQ-0010844 | 1004822 | A/C | 3.75E−06 | 32.3% |
|  |  | SQ-0000209 | 1020668 | G/T | 3.75E−06 | 32.3% |
|  |  | SQ-0006678 | 837806 | G/A | 3.78E−05 | 27.3% |
|  | 43 dpi | SQ-0000209 | 1020668 | G/T | 1.98E−06 | 33.7% |
|  |  | SQ-0010844 | 1004822 | A/C | 1.98E−06 | 33.7% |
|  |  | SQ-0006678 | 837806 | G/A | 3.45E−05 | 27.5% |
|  | 51 dpi | SQ-0010844 | 1004822 | A/C | 0.0016098 | 18.2% |
|  |  | SQ-0000209 | 1020668 | G/T | 0.0016098 | 18.2% |
|  | 58 dpi | SQ-0000209 | 1020668 | G/T | 0.0019356 | 17.7% |
|  |  | SQ-0010844 | 1004822 | A/C | 0.0019356 | 33.7% |
|  |  | SQ-0006678 | 837806 | G/A | 0.0100178 | 27.5% |
|  | 65 dpi | SQ-0000209 | 1020668 | G/T | 0.0001228 | 24.9% |
|  |  | SQ-0010844 | 1004822 | A/C | 0.0001228 | 24.9% |
|  |  | SQ-0006678 | 837806 | G/A | 0.0009669 | 19.8% |
| TLG BC2 | 36 dpi | SQ-0010844 | 1004822 | A/C | 6.03E−47 | 50.2% |
|  |  | SQ-0000209 | 1020668 | G/T | 4.41E−46 | 49.2% |
|  |  | SQ-0006678 | 837806 | G/A | 7.57E−46 | 49.2% |
| TLG BC1 | 36 dpi | SQ-0000209 | 1020668 | G/T | 9.80E−19 | 69.4% |
|  |  | SQ-0006678 | 837806 | G/A | 1.90E−16 | 64.5% |
|  |  | SQ-0010844 | 1004822 | A/C | 2.05E−16 | 64.4% |

Dpi = Days post inoculation, R = Resistant, S = Susceptible.

A QTL is inferred to be located close to the most significant marker within a given chromosome region (i.e., the marker with the lowest P-value or highest $R^2$ value). The P-value indicates the probability of obtaining results if the marker was not associated with variation for the trait. For example, a P-value of 0.01 indicates a 1% probability that these results would have been obtained in the absence of a marker-trait association. The lower the P-value is, the higher is the probability that a QTL truly exists in the region of the marker. $R^2$ value indicates the relative importance of a QTL in influencing a trait. It is the percent of the total phenotypic variance for the trait that is accounted for by a marker. The inventors concluded that the markers listed in the Table 3 were located closest to the resistance ToLCNDV QTL loci because they had the lowest P-value and the highest $R^2$ value. They have been able to identify that those markers have high association with the resistance to ToLCNDV in the 3 populations for all the tested conditions.

Genotyping analysis of the above described populations (BRV F1, AW026 (i.e. F1 population from cross between DGN and Menina Portugal), TLG BC1 and TLG BC2) is presented in Table 4 below. The analysis demonstrates that the resistant plants (i.e. plants having a resistance score above 7) harbor the resistant alleles for SNPs SQ-0000209, SQ-0006678 and SQ-0010844 at homozygous state.

TABLE 4

Genotyping analysis of QTL populations

| Plants | Resistance score | SQ-0006678 | SQ-0010844 | SQ-0000209 |
|---|---|---|---|---|
| Tarmino | 3 | A/A | C/C | T/T |
| DIVA | 1 | A/A | C/C | T/T |
| DGN | 3 | A/A | C/C | T/T |
| Menina Portugal | 9 | G/G | A/A | G/G |
| Menina Brasileira | 9 | G/G | A/A | G/G |
| BRV F1 | 5 | A/G | A/C | T/G |

TABLE 4-continued

Genotyping analysis of QTL populations

| Plants | Resistance score | SQ-0006678 | SQ-0010844 | SQ-0000209 |
|---|---|---|---|---|
| AW026 | 5 | A/G | A/C | T/G |
| TLG BC1 | 9 | G/G | A/A | G/G |
| TLG BC2 | 9 | G/G | A/A | G/G |

Resistant plants from the TLG BC2 population harboring the resistant alleles for the three markers have been then selfed and the resultant seeds obtained (i.e. BC2F3 population to which is referred "TLG") were deposited at the NCIMB (number NCIMB 42686).

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A *Cucurbita pepo* (*C. pepo*) plant tolerant of or resistant to Tomato Leaf Curl New Dehli Virus (ToLCNDV), wherein said plant comprises one Quantitative Trait Locus (QTL) associated with tolerance of or resistance to ToLCNDV on linkage group 11 (LG11), wherein said QTL on LG11 comprises markers: (1) SQ-0006678 (SEQ ID NO: 8) on one side and (ii) SQ-0010B44 (SEQ ID NO: 9) and/or SQ-0000209 (SEQ ID NO: 10) on the other side, and wherein said QTL associated with tolerance of or resistance to ToLCNDV is present in the genome of *C. pepo* variety TLG, a representative sample of seed of which has been deposited under NCIMB number 42686.

2. The *C. pepo* plant according to claim 1, wherein said plant is a progeny of said plant TLG.

3. A cell of a *C. pepo* plant according to claim 1.

4. A plant part obtained from a *C. pepo* plant according to claim 1.

5. A seed of a *C. pepo* plant, giving rise when grown up to a plant according to claim 1.

6. A method of breeding a plant of the genus *Cucurbita* tolerant of or resistant to Tomato Leaf Curl New Dehli Virus (ToLCNDV), the method comprising:
- (a) crossing a first cucurbit plant of the genus *Cucurbita* with a second plant of the genus *Cucurbita* to produce progeny plants of a subsequent generation, and selecting one or more progeny plants that contain the tolerance of or resistance to ToLCNDV from the progeny of the subsequent generation, wherein the first plant of the genus *Cucurbita* is tolerant of or resistant to ToLCNDV,
- (b) backcrossing the selected progeny plants that contain the tolerance of or resistance to ToLCNDV or selfed offspring thereof with the second cucurbit plant to produce backcross progeny plants,
- (c) selecting for backcross progeny plants that contain the tolerance of or resistance to ToLCNDV from the backcross progeny plants, and
- (d) repeating steps (b) and (c) one or more times in succession to produce selected second or higher backcross progeny plants that are tolerant of or resistant to ToLCNDV, wherein the progeny plants selected in (b) and (c) are selected by assaying for the presence of one or more of the markers SQ-0006678 (SEQ ID NO: 8), SQ-0010844 (SEQ ID NO: 9) and/or SQ-0000209 (SEQ ID NO: 10).

7. The method according to claim 6, wherein said first plant of the genus *Cucurbita* resistant to ToLCNDV is a *C. moschata* plant or a *C. pedatifolia* plant.

8. The method according to claim 7, wherein said *C. moschata* plant is 'Nigerian', 'Menina Portugal', 'Menina Brasileira', or a hybrid thereof.

9. The method according to claim 6, wherein said second plant of the genus *Cucurbita* is a *C. pepo* plant.

10. A selected *Cucurbita pepo* plant produced by the method according to claim 6, wherein said plant comprises one QTL associated with tolerant of or resistant to ToLCNDV on linkage group 11 (LG11), wherein said QTL on LG11 comprises markers: (1) SQ-0006678 (SEQ ID NO: 8) on one side and (ii) SQ-0010B44 (SEQ ID NO: 9) and/or SQ-0000209 (SEQ ID NO: 10) on the other side.

11. A plant, plant part, or plant cell derived from the plant of claim 10.

12. A seed produced by the plant of claim 11.

* * * * *

SEQUENCE LISTING

```
<160> NUMBER OF SEQ ID NOS: 10

<210> SEQ ID NO 1
<211> LENGTH: 2738
<212> TYPE: DNA
<213> ORGANISM: Tomato Leaf Curl New Delhi Virus

<400> SEQUENCE: 1
accgaatggc cgcgaaattt tttggtgggc cctgaaccaa tagaattcaa gttacatggc     60
ttatttagtg cgtggggacc aataaataga cttgctcacc aagtttagat ccacaaacat    120
gtgggatcca ttattgcacg aatttccgga aagcgtccat ggtctaaggt gcatgttagc    180
tgtaaaatat ctccaagaga ttgagaagtc ctattctcca gacacagtcg gctacgatct    240
tgtccgagat ctcattttag ttctccgagc caagaactat gtcgaagcga ccagcagata    300
tcatcatttc aactcccgca tcgaaggtac gccgacggct caacttcgac agccctatg    360 gaacccgtgc ctctgtcccc attgcccgcg tcacaaaagc aagggcctgg acgaacaggc    420
ccatgaacag aaaacccaga atgtacagaa tgtatagaag tcctgacgtg ccaaggggtt    480
gtgaaggccc ttgtaaggtg caatcgtttg aatcccggca cgatgtctcg catattggca    540
aagtcatgtg tgttagtgat gttactcgag gcaccggact cacacatcgc gtaggcaagc    600
gattttgtgt gaaatctgtc tatgtactgg gaaaaatatg gatggatgaa aatatcaaaa    660
ctaaaaatca tactaatagt gttatgttct ttcttgttcg tgaccggcgt ccaaccggaa    720
cccctcaaga ttttggggaa gttttcaata tgtttgataa tgaacctagc acagccacgg    780
tgaagaacat gcatcgtgat cgttatcaag tcttacggaa gtggcatgct actgtgacgg    840
gaggaacgta tgcatcaagg gagcaagcat tagttaggaa gtttgttagg gttaataatt    900
atgttgttta caatcaacaa gaggccggca agtatgagaa tcatactgaa aatgcattaa    960
tgttgtatat ggcctgtact catgcatcaa atcctgtgta tgctactttg aaaatccgga   1020
tctattttta tgattcggtc acaaattaat atatattgat ctttacatca tatgttgtcc   1080
atacatcaat cgttttatgc aagacattat ctaaaacatg ataaacagct cttattacat   1140
tacaaatgcc gactacacca agcatattta ggtacttaag gacctgcgtt ctaaaaaccc   1200
tcaagaaaat cccagtcgga gggcgtaagc ccgtccagat ttggaaagtt agaaaacact   1260
tgtgaagccc cagagctttc cgcaggttgt ggttgaactg tacttggact ttgattatgt   1320
cgtgattggt caggcacggt ctgctgtcgt gtttcaatac tttgaaatac agggatttg   1380 gtacgtccca gataaagacg ccactctctt ctcgatccgc agtgatgtac tccctgtgc   1440 gtgaatccgt gatcatggca attgatcgat atgtagtagg aacaaccgca ctgcagatca   1500
actcgcctcc tgcgaatgtt cttcttcttc ttctggggga gcgatgtttt cgcgactgga   1560
atagagtggt tcttcgagtg tgatgaagac tgcattcttg attgcccact gcttcagtgc   1620
```

-continued

```
tgcattttttt tcttcgtcaa gatattctttt ataactgctg tttggtcctt cattgcacag    1680
gaagatagtg ggaattccac ctttaatcat gacaggcttt ccgtacttcg tgttgctttg    1740
ccagtcacgt tgggccccca tgaattcttt aaaatgcttt agatagtggg gatcaacgtc    1800
gtcaatgacg ttgtaccagg catcattgct ataaactttt gggctaagat ccagatgacc    1860
acacaaataa ttgtggggtc ctaaacaacg cgcccacatt gttttgcccg tcctactatc    1920
gccctgtatg actatgctta ttggtcttaa aggccgcgca gckgaacaca ccacattaca    1980
tttggcccaa tcgacgagat ctgcaggaac tctgtcgaag gatgaaatcg aaaaggaga    2040 aacataaacc tccgaacgag tctggaaaat gcgatctaaa ttattaatta aattatgaaa    2100
ctgcagaaca taatcttttg gtgctagttc ctttaaaacc tttaacgcat ctgtcttgtt    2160
tccagtgtta attgcctgag catatgcatc gttggccgtt tgttgaccac cacgagcaga    2220
tcgtccatcg atctgaaaaa caccccattc tagaacgtct ccgtctttgt cgatgtatgc    2280
cttgacgtcc gacgctgatt tagctccctg aatgttcgga tggaaatgtg ctgccctact    2340
tggggacacc aagtcgaaga atctgttatt cttgcactgg aatttccctt cgaattggac    2400
gagaacatgg atatgcggag acccatcctc gtgaagctct ctacagatct tgatgaattt    2460
cttcgaagtt ggggtttcta gggtttgtaa ttgggaaagt gcctcttcct ttgtaagaga    2520
gcacttcgga tacgtgagga aatagttttt ggcatttatt ctaaaacgac ttggcggagc    2580
cataaaaagt gtcgtttcga tctggtgtct ctcaacttcc tgtatgtaat tggtgtctgg    2640
agtcccatat ataggtaaga cactaaatgg cagaattgta attttgaaga gaaaattact    2700
ttaaatcaaa tttcaaaagc ggccattcgt ataatatt                             2738
```

<210> SEQ ID NO 2
<211> LENGTH: 2738
<212> TYPE: DNA
<213> ORGANISM: Tomato Leaf Curl New Dehli Virus

<400> SEQUENCE: 2

```
accgaatggc cgcgaaattt tttggtgggc cctgaaccaa tagaattcaa gttacatggc      60
ttatttagtg cgtggggacc aataaataga cttgctcacc aagtttagat ccacaaacat     120
gtgggatcca ttattgcacg aatttccgga aagcgtccat ggtctaaggt gcatgttagc     180
tgtaaaatat ctccaagaga ttgagaagtc ctattctcca gacacagtcg gctacgatct     240
tgtccgagat ctcattttag ttctccgagc caagaactat gtcgaagcga ccagcagata     300
tcatcatttc aactcccgca tcgaaggtac gccgacggct caacttcgac agcccctatg     360
gaacccgtgc ctctgtcccc attgcccgcg tcacaaaagc aagggcctgg acgaacaggc     420
ccatgaacag aaaacccaga atgtacagaa tgtatagaag tcctgacgtg ccaagggggtt     480 gtgaaggccc ttgtaaggtg caatcgtttg aatcccggca cgatgtctcg catattggca     540
aagtcatgtg tgttagtgat gttactcgag gcaccggact cacacatcgc gtaggcaagc     600
gattttgtgt gaaatctgtc tatgtactgg gaaaaatatg gatggatgaa aatatcaaaa     660
ctaaaaatca tactaatagt gttatgttct ttcttgttcg tgaccggcgt ccaaccggaa     720
cccctcaaga ttttggggaa gttttcaata tgtttgataa tgaacctagc acagccacgg     780
tgaagaacat gcatcgtgat cgttatcaag tcttacggaa gtggcatgct actgtgacgg     840
gaggaacgta tgcatcaagg gagcaagcat tagttaggaa gtttgttagg gttaataatt     900
atgttgttta caatcaacaa gaggccggca agtatgagaa tcatactgaa aatgcattaa     960
```

```
tgttgtatat ggcctgtact catgcatcaa atcctgtgta tgctactttg aaaatccgga      1020
tctattttta tgattcggtc acaaattaat atatattgat ctttacatca tatgttgtcc      1080
atacatcaat cgttttatgc aagacattat ctaaaacatg ataaacagct cttattacat      1140
tacaaatgcc gactacacca agcatattta ggtacttaag gacctgcgtt ctaaaaaccc      1200
tcaagaaaat cccagtcgga gggcgtaagc ccgtccagat atggaaagtt agaaaacact      1260
tgtgaagccc cagagctttc gcaggttgt ggttgaactg tacttggatt ttgattatgt       1320
cgtgattggt caggcacggt ctgctgtcgt gtttcaatac tttgaaatac aggggatttg      1380
gtacgtccca gataaagacg ccactctctg ctcgatccgc agtgatgtac tcccctgtgc      1440
gtgaatccgt gatcatggca attgatcgat atgtagtagg aacaaccgca ctgcagatca      1500
actcgcctcc tgcgaatgtt cttcttcttc tctgggggga gcgatgtttt cgcgactgga      1560
atagagtggt tcttcgagtg tgatgaagac tgcattcttg attgcccact gcttcagtgc      1620 tgcattttt tcttcgtcaa gatattcttt ataactgctg tttggtcctt cattgcacag       1680
gaagatagtg ggaattccac ctttaatcat gacaggcttt ccgtactttg tgttgctttg      1740
ccagtcacgt tgggccccca tgaattcttt aaagtgcttt agatagtggg gatcaacgtc      1800
gtcaatgacg ttgtaccagg catcattgct ataaactttt gggctaagat ccagatgacc      1860
acacaaataa ttgtggggtc ctaaacaacg cgcccacatt gttttgcccg tcctactatc      1920
tccctctatg actatgctta ttggtcttaa tggccgcgca gcggaacaca ccacattaca      1980
tttggcccaa tcgacgagat ctgcaggaac tctgtcgaag gatgaaatcg aaaaaggaga      2040
aacataaacc tccgaacgag tctggaaaat gcgatctaaa ttattaatta aattatgaaa      2100
ctgcagaaca taatcttttg gtgctagttc ctttaaaacc tttaacgcat ctgtcttgtt      2160
tccagtgtta attgcctgag catatgcatc gttggccgtt tgttgaccac cacgagcaga      2220
tcgtccatcg atctgaaaaa cacccccattc tagaacgtct ccgtctttgt cgatgtatgt     2280
cttgacgtcc gacgctgatt tagctccctg aatgttcgga tggaaatgtg ctgccctact     2340
tggggacacc aagtcgaaga atctgttatt cttgcactgg aatttcccctt cgaattggac    2400 gagaacatgg atatgcggag acccatcctc gtgaagctct ctacagatct tgatgaattt     2460
cttcgaagtt ggggtttcta gggtttgtaa ttgggaaagt gcctcttcct ttgtaagaga     2520
gcacttcgga tacgtgagga aatagttttt tgcatttatt ctaaaacgac ttggcggagc     2580
cataaaacgt gtcgtttcga tctggtgtct ctcaacttcc tgtatgtaat tggtgtctgg     2640
agtcccatat ataggtaaga cactaaatgg cagaattgta attttgaaga gaaaattact     2700
ttaattcaaa tttcaaaagc ggccattcgt ataatatt                              2738
```

<210> SEQ ID NO 3
<211> LENGTH: 970
<212> TYPE: DNA
<213> ORGANISM: Tomato Leaf Curl New Dehli Virus

<400> SEQUENCE: 3

```
tttggctgtg aaaggcccat gtaaggtgca atcgtttgaa tcccggcacg atgtctcgca        60
tattggcaaa gtcatgtgtg ttagtgatgt tactcgaggc accggactca cacatcgcgt       120
aggcaagcga ttttgtgtga atctgtctta tgtactggga aaaatatgga tggatgaaaa       180
tatcaaaact aaaaatcata ctaatagtgt tatgttcttt cttgttcgtg accggcgtcc       240
aaccggaacc cctcaagatt ttggggaagt tttcaatatg tttgataatg aacctagcac       300
agccacggtg aagaacatgc atcgtgatcg ttatcaagtc ttacggaagt ggcatgctac       360
```

-continued

```
tgtgacggga ggaacgtatg catcaaggga gcaagcatta gttaggaagt ttgttagggt    420
taataattat gttgtttaca atcaacaaga ggccggcaag tatgagaatc atactgaaaa    480
tgcattaatg ttgtatatgg cctgtactca tgcatcaaat cctgtgtatg ctactttgaa    540
aatccggatc tattttatg attcggtcac aaattaat atattgatct ttacatcata    600
tgttgtccat acatcaatcg ttttatgcaa gacattatct aaaacatgat aaacagctct    660
tattacatta caaatgccga ctacaccaag catatttagg tacttaagga cctgcgttct    720
aaaaaccctc aagaaaatcc cagtcggagg gcgtaagccc gtccagattt ggaaagttag    780
aaaacacttg tgaagcccca gagctttccg caggttgtgg ttgaactgta cttggactt    840 gattatgtcg tgattggtca ggcacggtct gctgtcgtgt ttcaatactt tgaaatacag    900
gggatttggt acgtcccaga taaagacgcc actctctgct cgatccgcag tgatgtactc    960
ccctgtgcgt                                                          970
```

<210> SEQ ID NO 4
<211> LENGTH: 20
<212> TYPE: DNA
<213> ORGANISM: Unknown
<220> FEATURE:
<223> OTHER INFORMATION: Forward primer

<400> SEQUENCE: 4
ggctgtgaag gcccatgtaa                                               20

<210> SEQ ID NO 5
<211> LENGTH: 19
<212> TYPE: DNA
<213> ORGANISM: Unknown
<220> FEATURE:
<223> OTHER INFORMATION: Reverse primer

<400> SEQUENCE: 5
atggattcac gcacagggg                                                19

<210> SEQ ID NO 6
<211> LENGTH: 23
<212> TYPE: DNA
<213> ORGANISM: Unknown
<220> FEATURE:
<223> OTHER INFORMATION: Forward primer

<400> SEQUENCE: 6
ttggatccat ggcgaagcga cca                                           23

<210> SEQ ID NO 7
<211> LENGTH: 23
<212> TYPE: DNA
<213> ORGANISM: Unknown
<220> FEATURE:
<223> OTHER INFORMATION: Reverse primer

<400> SEQUENCE: 7
aagagctctt aatttgtgac cga                                           23

<210> SEQ ID NO 8
<211> LENGTH: 71
<212> TYPE: DNA
<213> ORGANISM: Unknown
<220> FEATURE:
<223> OTHER INFORMATION: Flanking sequence of marker SQ-0006678
<220> FEATURE:

```
<221> NAME/KEY: misc_feature
<222> LOCATION: (1)..(71)
<223> OTHER INFORMATION: allele G: Resistant allele
<220> FEATURE:
<221> NAME/KEY: misc_feature
<222> LOCATION: (1)..(71)
<223> OTHER INFORMATION: allele A: Susceptible allele

<400> SEQUENCE: 8
gttgtaagtc cagcaatagc accaacgctt atcaaraaag aaacaaattt caagcctttg    60
gatgtaaaag c                                                         71

<210> SEQ ID NO 9
<211> LENGTH: 71
<212> TYPE: DNA
<213> ORGANISM: Unknown
<220> FEATURE:
<223> OTHER INFORMATION: Flanking sequence of marker SQ-0010844
<220> FEATURE:
<221> NAME/KEY: misc_feature
<222> LOCATION: (1)..(71)
<223> OTHER INFORMATION: allele G: Resistant allele
<220> FEATURE:
<221> NAME/KEY: misc_feature
<222> LOCATION: (1)..(71)
<223> OTHER INFORMATION: allele A: Susceptible allele

<400> SEQUENCE: 9
aaaagagaaa gttggaggac tgagttgcca agggcmggcc tgggatctga agtcattgtg    60
aaaatgaaaa a                                                         71

<210> SEQ ID NO 10
<211> LENGTH: 155
<212> TYPE: DNA
<213> ORGANISM: Unknown
<220> FEATURE:
<223> OTHER INFORMATION: Flanking sequence of marker SQ-0000209
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (1)..(155)
<223> OTHER INFORMATION: allele G: Resistant allele
<220> FEATURE:
<221> NAME/KEY: misc_feature
<222> LOCATION: (1)..(155)
<223> OTHER INFORMATION: allele A: Susceptible allele

<400> SEQUENCE: 10
ttaacaccac cgattctcag ctccagtagc aagaccagta gactgccatg gaactccatc    60
gttctcagag gaaatcttcc accgcnacca nttcctcgac cactcttcca ctctatcgct   120
cmgctcctcc tctcgaagtc aggcttgaag aattc                              155
```